US008563690B2

(12) United States Patent
Du et al.

(10) Patent No.: US 8,563,690 B2
(45) Date of Patent: Oct. 22, 2013

(54) MODULATION OF PLATELET AGGREGATION

(75) Inventors: Xiaoping Du, Willowbrook, IL (US); Xiaodong Xi, Shanghai (CN)

(73) Assignee: The Board of Trustees of the University of Illinois, Urbana, IL (US)

( * ) Notice: Subject to any disclaimer, the term of this patent is extended or adjusted under 35 U.S.C. 154(b) by 805 days.

(21) Appl. No.: 12/611,446

(22) Filed: Nov. 3, 2009

(65) Prior Publication Data

US 2010/0260828 A1  Oct. 14, 2010

Related U.S. Application Data

(60) Provisional application No. 61/110,740, filed on Nov. 3, 2008.

(51) Int. Cl.
*A61K 38/06* (2006.01)

(52) U.S. Cl.
USPC .......................................... 530/331; 514/21.9

(58) Field of Classification Search
None
See application file for complete search history.

(56) References Cited

U.S. PATENT DOCUMENTS

| | | | |
|---|---|---|---|
| 4,529,596 A | 7/1985 | Aubert et al. | |
| 5,036,156 A | 7/1991 | Bouisset et al. | |
| 5,137,912 A * | 8/1992 | Teng et al. | 514/463 |
| 5,576,328 A | 11/1996 | Herbert et al. | |
| 6,080,875 A | 6/2000 | Castro et al. | |
| 6,096,707 A | 8/2000 | Heino et al. | |
| 6,180,793 B1 | 1/2001 | Bakonyi et al. | |
| 6,210,913 B1 | 4/2001 | Phillips et al. | |
| 6,258,961 B1 | 7/2001 | Bakonyi et al. | |
| 6,399,345 B2 * | 6/2002 | Bandman et al. | 435/191 |
| 6,413,544 B1 * | 7/2002 | Smyth-Templeton et al. | 424/450 |
| 6,818,427 B1 * | 11/2004 | Palombella et al. | 435/194 |
| 6,911,335 B2 * | 6/2005 | Kapeller-Libermann et al. | 435/226 |
| 2006/0275312 A1 * | 12/2006 | Chua et al. | 424/184.1 |
| 2007/0059799 A1 * | 3/2007 | Sette et al. | 435/69.1 |
| 2007/0066534 A1 * | 3/2007 | Jackson et al. | 514/13 |

FOREIGN PATENT DOCUMENTS

| | | |
|---|---|---|
| EP | 0917462 A1 | 5/1999 |
| WO | WO-9711718 A1 | 4/1997 |
| WO | WO-9816241 A1 | 4/1998 |
| WO | WO-0179144 A2 | 10/2001 |
| WO | WO-03031476 A1 | 4/2003 |
| WO | WO-2005056575 A2 | 6/2005 |

OTHER PUBLICATIONS

Loo et. al. A study of Src SH2 Domain Protein- Phosphopeptide Binding Interactions by Electrospray Ionization Mass Spectometry, J. Am. Soc. Mass Spec. vol. 8, 234-243, 1997.*
Krissansen et. al. A pseudosymmetric cell adhesion regulatory domain in the β7 tail of the integrin α4β7 that interacts with focal adhesion kinase and src. Eur. J. Immunol. 36: 2203-2214, (2006).*
Vingradova et. al. A structural basis for integrin activation by the cytoplasmic tail of the αIIb-subunit, PNAS, vol. 97, No. 4, (Feb. 15, 2000).*
Su et. al. RGT, a synthetic peptide corresponding to the integrin β3 cytoplasmic C-terminal sequence, selectively inhibits outside-in signaling in the human platelets by disrupting the interaction of integrin αIIbβ3 with Src kinase, Blood, vol. 112, No. 3, 592-601, (2008).*
Angelillo-Scherrer et al., "Role of Gas6 receptors in platelet signaling during thrombus stabilization and implications for antithrombotic therapy," *J. Clin. Invest.* 115:237-246, 2005.
Arias-Salgado et al., "Src kinase activation by direct interaction with the integrin beta cytoplasmic domain," *Proc. Natl. Acad. Sci. U.S.A.*, 100:13298-13302, 2003.
Arias-Salgado et al., "Specification of the direction of adhesive signaling by the integrin beta cytoplasmic domain," J. Biol. Chem., 280:29699-29707, 2005.
Bangham et al., J. Mol. Biol., 13(1):253-259, 1965.
Bassler et al., "A mechanistic model for paradoxical platelet activation by ligand-mimetic alphaIIb beta3 (GPIIb/IIIa) antagonists," *Arterioscler. Thromb. Vasc. Biol.*, 27:e9-15, 2007.
Dai et al., "A critical role for 14-3-3zeta protein in regulating the VWF binding function of platelet glycoprotein Ib-IX and its therapeutic implications," *Blood*, 106:1975-1981, 2005.
Deemer and Uster, In: Liposome Preparation: Methods and Mechanisms, Ostro (Ed.), Liposomes, 1983.
Flevaris et al., "A molecular switch that controls cell spreading and retraction," *J. Cell. Biol.* 179:553-565, 2007.
Ginsberg et al., "Inhibition of fibronectin binding to platelets by proteolytic fragments and synthetic peptides which support fibroblast adhesion," J. Biol. Chem., 260:3931-3936, 1985.
Hers et al., "Inhibition of platelet integrin alpha(IIb)beta(3) by peptides that interfere with protein kinases and the beta(3) tail," Arterioscler. Thromb. Vasc. Biol., 20:1651-1660, 2000.
Hynes, "Integrins: bidirectional, allosteric signaling machines," Cell, 110:673-687, 2002.
Ginsberg MH, Partridge A, Shattil SJ. Integrin regulation. *Curr. Opin. Cell Biol.* 2005;17:509-516.
Gregoriadis, In: Drug Carriers in Biology and Medicine, Gregoriadis (Ed.), 287-341, 1979.
Larkin et al., "ICIn, a novel integrin alphaIIbbeta3-associated protein, functionally regulates platelet activation," *J. Biol. Chem.*, 279:27286-27293, 2004.

(Continued)

Primary Examiner — Cecilia J Tsang
Assistant Examiner — Jeanette Lieb
(74) Attorney, Agent, or Firm — Marshall, Gerstein & Borun LLP

(57) ABSTRACT

Methods and compositions for inhibition of platelet cell aggregation are described. In particular, compositions comprising cell permeant RGT peptides, such as RGT bound to a lipid moiety are provided. Compositions may be used in the treatment and prevention of clot related diseases such as stroke and myocardial infarction.

35 Claims, 8 Drawing Sheets

(56) References Cited

OTHER PUBLICATIONS

Law et al., "Outside-in integrin signal transduction. Alpha IIb beta 3-(GP IIb IIIa) tyrosine phosphorylation induced by platelet aggregation," *J. Biol. Chem.* 271:10811-10815, 1996.

Law et al., "Integrin cytoplasmic tyrosine motif is required for outside-in alphaIIbbeta3 signalling and platelet function," *Nature*, 401:808-811, 1999.

Li et al. "A mitogen-activated protein kinase-dependent signaling pathway in the activation of platelet integrin alpha IIbbeta3," *J. Biol. Chem.*, 276:42226-42232, 2001.

Li et al., "A platelet secretion pathway mediated by cGMP-dependent protein kinase," *J. Biol. Chem.* 279:42469-42475, 2004.

Liu et al., "Identification of a functionally important sequence in the cytoplasmic tail of integrin beta 3 by using cell-permeable peptide analogs," *Proc. Natl. Acad. Sci. U.S.A.*, 93:11819-11824, 1996.

Liu et al. "The beta3 subunit of the integrin alphaIIbbeta3 regulates alphaIIb-mediated outside-in signaling," *Blood*, 105:4345-4352, 2005.

Litjens et al., "Involvement of the beta3 $E^{749}ATSTFTN^{756}$ region in stabilizing integrin alphaIIbbeta3-ligand interaction," *J. Thromb. Haemost.*, 1:2216-2224, 2003.

Litjens et al. "Cytoplasmic regions of the beta3 subunit of integrin alphaIIbbeta3 involved in platelet adhesion on fibrinogen under flow conditions," *J. Thromb. Haemost.* 1:2014-2021, 2003.

Martin et al., "A palmitylated peptide derived from the glycoprotein Ib beta cytoplasmic tail inhibits platelet activation," *J. Thromb. Haemost.*, 1:2643-2652, 2003.

Obergfell et al., "Coordinate interactions of Csk, Src, and Syk kinases with [alpha]IIb[beta]3 initiate integrin signaling to the cytoskeleton," *J. Cell. Biol.*, 157:265-275, 2002.

Osdoit et al., "Fibrin clot retraction by human platelets correlates with alpha(IIb)beta(3) integrin-dependent protein tyrosine dephosphorylation," *J. Biol. Chem.*, 276:6703-6710, 2001.

Phillips et al., "Therapeutic approaches in arterial thrombosis," *J. Thromb. Haemost.*, 3:1577-1589, 2005.

Podolnikova et al., "Identification of a novel binding site for platelet integrins alpha IIb beta 3 (GPIIbIIIa) and alpha 5 beta 1 in the gamma C-domain of fibrinogen," *J. Biol. Chem.*, 278:32251-32258, 2003.

Prevost et al., "Signaling by ephrinB1 and Eph kinases in platelets promotes Rap1 activation, platelet adhesion, and aggregation via effector pathways that do not require phosphorylation of ephrinB1," *Blood* 103:1348-1355, 2004.

Prevost et al., "Eph kinases and ephrins support thrombus growth and stability by regulating integrin outside-in signaling in platelets," *Proc. Natl. Acad. Sci. U.S.A.*, 102:9820-9825, 2005.

Shattil et al., "Integrin signaling: the platelet paradigm," *Blood* 91:2645-2657, 1998.

Szoka and Papahadjopoulos, *Proc. Natl. Acad. Sci. U.S.A.*, 75:4194-4198, 1978.

Stephens et al., "A sequence within the cytoplasmic tail of GpIIb independently activates platelet aggregation and thromboxane synthesis," *J. Biol. Chem.* 273:20317-20322, 1998.

Su et al., "RGT, a synthetic peptide corresponding to the integrin beta 3 cytoplasmic C-terminal sequence, selectively inhibits outside-in signaling in human platelets by disrupting the interaction of integrin alpha IIb beta 3 with Src kinase," *Blood*, 112:592-602, 2008.

Tadokoro et al., "Talin binding to integrin beta tails: a final common step in integrin activation," *Science* 302:103-106, 2003.

Tsuboi, "Calcium integrin-binding protein activates platelet integrin alpha IIbbeta 3," *J. Biol. Chem.*, 277:1919-1923, 2002.

Vinogradova et al., "A structural basis for integrin activation by the cytoplasmic tail of the alpha IIb-subunit," *Proc. Natl. Acad. Sci. U.S.A.*, 97:1450-1455, 2000.

Vinogradova et al., "A structural mechanism of integrin alpha(IIb)beta(3) "inside-out" activation as regulated by its cytoplasmic face," *Cell*, 110:587-597, 2002.

Wang et al., "Platelet alpha2beta1 integrin activation: contribution of ligand internalization and the alpha2-cytoplasmic domain," *Blood*, 102:1307-1315, 2003.

Xi et al., "Critical roles for the COOH-terminal NITY and RGT sequences of the integrin beta3 cytoplasmic domain in inside-out and outside-in signaling," *J. Cell. Biol.*, 162:329-339, 2003.

Xi et al. "Tyrosine phosphorylation of the integrin beta3 subunit regulates beta3 cleavage by calpain," *J. Biol. Chem.*, 281:29426-29430, 2006.

Basani et al., RGD-containing peptides inhibit fibrinogen binding to platelet alpha(IIb)beta3 by inducing an allosteric change in the amino-terminal portion of alpha(IIb). *J. Biol. Chem.*, 276(17):13975-81 (2001).

\* cited by examiner

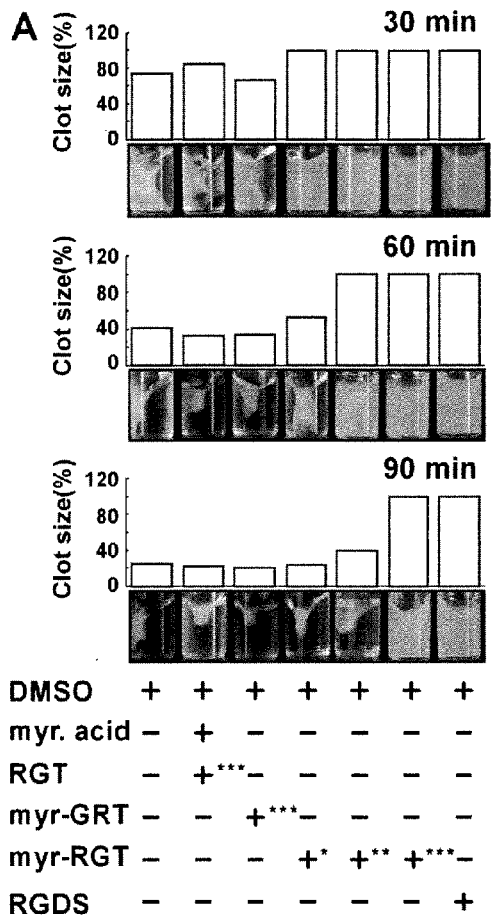
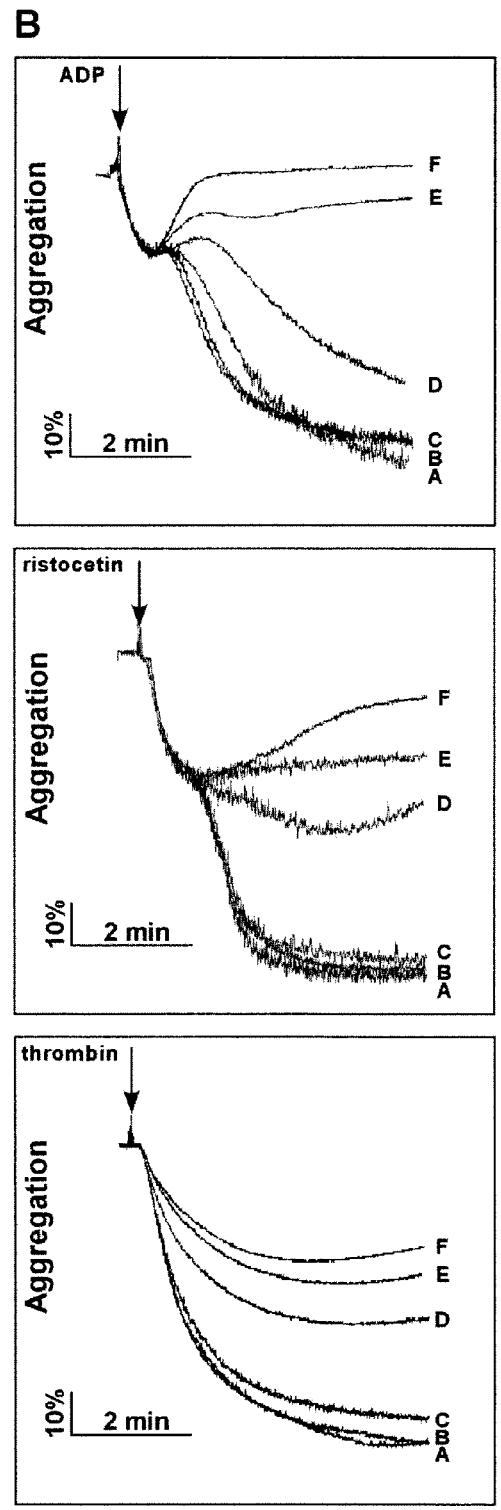
FIG. 3A-B

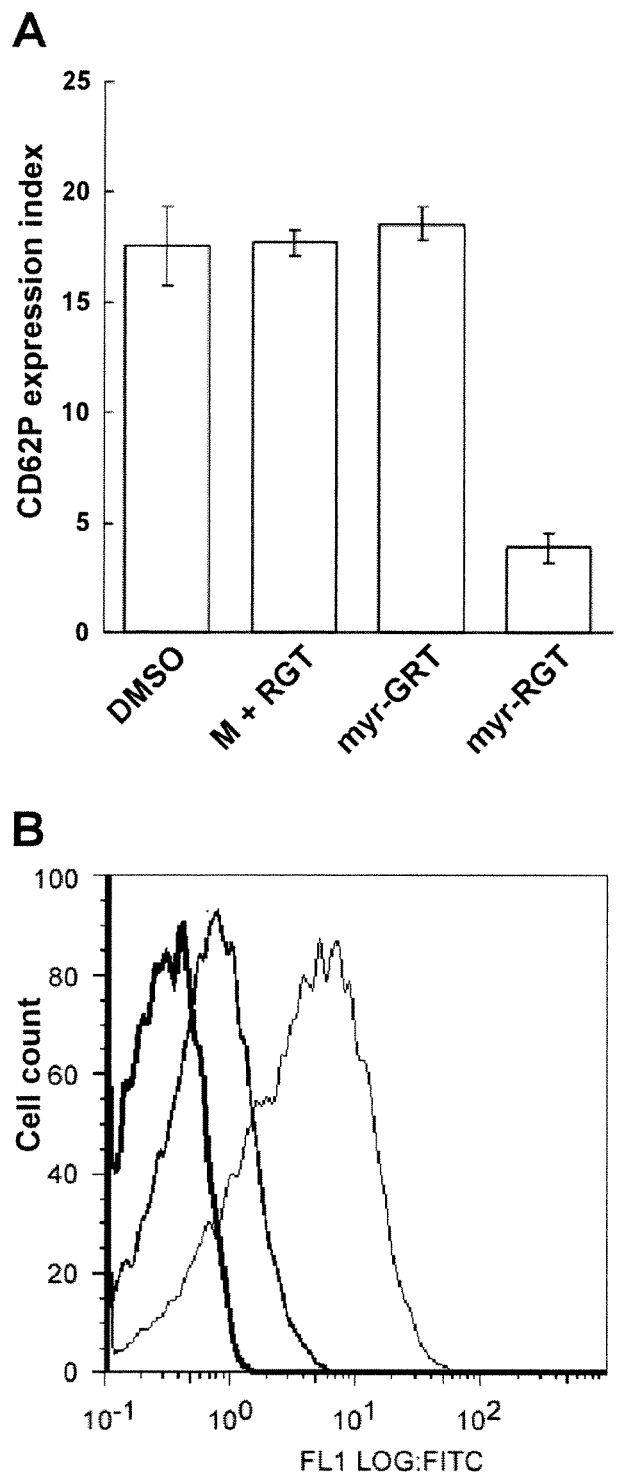
FIG. 5A-B

FIG. 7A-D

MODULATION OF PLATELET AGGREGATION

PRIORITY

This application claims priority to U.S. Provisional Application No. 61/110,740, filed Nov. 3, 2008, which is hereby incorporated by reference in its entirety.

GOVERNMENT INTERESTS

This invention was made with U.S. government support under grant numbers HL062350, HL080264, and HL68819 awarded by the National Institutes of Health. The U.S. government has certain rights in the invention.

BACKGROUND OF THE INVENTION

Over the last decade, considerable effort has focused on the prevention and treatment of aberrant blood clot (thrombus) formation which can result in ischemic events and other complications. Prevention of ischemic events could significantly reduce the prevalence diseases such as of acute myocardial infarction, angina, complications following angioplasty, restenosis, thrombotic stroke, ischemic neurological deficits and other ischemic disorders.

Histological studies of vascular injuries have demonstrated the importance of platelets, adenosine diphosphate (ADP), smooth muscle cells and thrombosis in atherosclerotic cardiovascular, cerebrovascular and peripheral arterial diseases. However, while a variety of anti-thrombotic drugs have been available, the primary mechanisms of platelet aggregation were not well understood and this lack of understanding has prevented the development of additional effective therapeutics for ischemic disease conditions.

Integrins mediate cell adhesion and transduce signals that are critical in the dynamic regulation of cell adhesion, spreading, migration, and proliferation. Thus, integrin activity is central to regulation of platelet adhesion and clot formation (Hynes, 2002 and Ginsberg et al., 2005). Bidirectional signaling of integrins is exemplified in the prototype platelet integrin, αIIbβ3. Inside-out signaling of integrin αIIbβ3 requires talin binding to the cytoplasmic domain of αIIbβ3, which leads to conformational changes, which, in turn, propagate to the extracellular ligand binding domain, activate the ligand binding function (Tadokoro et al., 2003 and Vinogradova et al., 2002). Ligand binding to αIIbβ3 not only forms adhesive bonds, but also induces outside-in signaling leading to platelet spreading, secretion, amplification of platelet aggregation and subsequent clot retraction (Shattil et al., 1998). It is known that outside-in signaling of integrin αIIbβ3 requires phosphorylation of the β3 subunit cytoplasmic domain at $Y^{747}$ and $Y^{759}$ (Law et al., 1999). It has also been reported using multiple Src family protein tyrosine kinases-deficient mouse models that Src plays an important role in the integrin outside-in signaling (Obergfell et al., 2002). However, the exact molecular events and the direct requirement for this kinase in β3 tyrosine phosphorylation in human platelets remain to be established.

The cytoplasmic domain of the β3 subunit is critical in integrin bidirectional signaling. Inside-out signaling requires the membrane proximal region of β3, including the highly conserved $N^{744}PXY^{747}$ motif which directly interacts with the talin head domain allowing receptor activation. It has been shown that the C-terminus of β3 interacts with Src, an interaction that is important in integrin outside-in signaling leading to cell spreading, and that two residues in the β3 cytoplasmic tail, R760 and T762, are necessary for Src binding (Arias-Salgado et al., 2005). Furthermore, deletion of the C-terminal RGT amino acidsequence of β3 abolishes Src binding (Flevaris et al., 2007). However, it was not known which amino acid sequences are sufficient for Src binding. Moreover, in human platelets, the precise functional role of the $R^{760}GT^{762}$ residues in outside-in signaling was not understood.

Thus, there exists a need in the art to develop materials and methods which can be used to modulate platelet aggregation. The instant disclosure elucidates aspects of integrin β3-Src signaling in platelet cells and discloses compositions to disrupt platelet cell signaling. Thus, the instant disclosure addresses a deficit in the art by providing methods to reduce platelet aggregation by disrupting intracellular signaling in platelets.

SUMMARY

In a first embodiment, a method is provided for inhibiting platelet aggregation in a subject comprising administering to the subject a membrane permeant composition comprising an RGT peptide, the membrane permeant composition having the activity of inhibiting binding of Src to integrin β3 in a platelet cell, the composition administered in an amount effective to inhibit platelet aggregation. In some further aspects, there is provided a method for reducing the size of a blood clot in a subject comprising administering to the subject a membrane permeant composition comprising an RGT peptide, the membrane permeant composition having the activity of inhibiting binding of Src to integrin β3 in a platelet cell, the composition administered in an amount effective to reduce the size of a blood clot.

For the purposes of this disclosure, permeant compositions comprising an RGT peptide are referred to as RGT peptide compositions. In some aspects, an RGT peptide composition is further defined as a composition which inhibits or reduces phosphorylation of integrin β3 in a platelet cell or alternatively a composition which inhibits or reduces phosphorylation at residues $Y^{747}$ or $Y^{759}$ of integrin β3 in a platelet cell. The term RGT peptide refers to a peptide sequence comprising the amino acid sequence arginine-glycine-threonine (RGT). In one aspect, an RGT amino acid sequence is C-terminally disposed in the RGT peptide (i.e., wherein the threonine residue is the carboxyl-terminal residue on the RGT peptide). In certain aspects an RGT peptide is defined as consisting of an amino acid sequence of less than 50, 40, 30, 25, 20, 15 or 10 amino acids. An RGT peptide in some cases consists of only the amino acids R, G and T or, in other aspects, the peptide comprises additional amino acids. For example, in one aspect, an RGT peptide comprises two or more repeats of the RGT sequence and such repeats, optionally, are separated by a linker amino acid sequence. Alternatively, the direct repeats include no additional intervening sequence.

As used herein the term membrane permeant composition refers to a composition which can traverse, actively or passively, a lipid bilayer such as the plasma membrane of a platelet cell. A variety of compositions are known in the art which are used in a membrane permeant composition. For example, in one aspect, an RGT peptide is associated with or covalently attached to a membrane permeant polypeptide, associated with a liposome or associated with a hydrophobic moiety. Membrane permeant polypeptides (also termed protein transduction domains or cell-penetrating peptides) include, but are not limited to, HIV tat domains, Antennapedia, herpes simplex virus (HSV) VP22 proteins and polypeptides comprising poly-arginine or poly-lysine domains. In certain aspects, a membrane permeant composition comprises an RGT peptide having a hydrophobic moiety such as a lipid covalently bound thereto. For example, in one aspect, an RGT peptide is covalently linked to a fatty acid such as a saturated or unsaturated fatty acid. Moreover, in some aspects, a RGT peptide composition further comprises additional components such as a pharmaceutically acceptable carrier, excipient or buffer and/or additional therapeutic agents.

A skilled artisan will recognize that inhibiting platelet aggregation is useful, for example, for inhibiting clot formation in a subject and is therefore useful in treating a variety of disease conditions. For example, in one aspect, an RGT peptide composition is administered as a therapy or prophylaxis to prevent a primary and/or secondary ischemic event, such as angina, reocclusion after percutaneous transluminal coronary angioplasty, restenosis, thrombotic stroke, transient ischemic attack, reversible ischemic neurological deficit, myocardial infarction or intermittent claudication. Thus, a subject for treatment by the instant methods is, in one aspect, a subject that is at risk for an ischemic event such as a subject having arterial sclerosis, a subject which has suffered from a previous ischemic event or a subject with a family history of ischemic events. In another aspect, RGT peptide compositions is administered to a subject having a blood clot in an amount sufficient to reduce the size or mass of the blood clot. For instance, in various aspects, RGT peptide compositions are used in the treatment (prevention) of pulmonary embolism, venous thrombosis, deep vein thrombosis, portal vein thrombosis, renal vein thrombosis, jugular vein thrombosis, Budd-Chiari syndrome, Paget-Schroetter disease, cerebral venous sinus thrombosis, arterial thrombosis, thrombotic stroke or myocardial infarction.

Membrane permeant compositions are administered to a subject by a variety of routes including but not limited oral, nasal, buccal, rectal, vaginal or topical. Alternatively, administration is by orthotopic, intradermal subcutaneous, intramuscular, intraperitoneal, or intravenous injection. Compositions will normally be administered as pharmaceutically acceptable compositions that include physiologically acceptable carriers, buffers or other excipients. In certain aspects, continuous perfusion over hours or days or even longer periods via a catheter or by use of a pump or reservoir comprising therapeutic composition is desirable. Thus, in certain embodiments, therapeutic compositions are administered continuously over extended periods of time to provide a serum concentration that is maintained with-in constant range. In one aspect, RGT peptide compositions are delivered to the blood stream such as by intravenous administration. In certain aspects, methods comprise administering a specific dose of an RGT peptide composition such as an amount that results in a serum concentration (or in some aspects an intracellular concentration) of greater than about 50, 100, 200, 250 or 500 μM of an RGT peptide. Compositions are delivered systemically or locally. For example, in one aspect, compositions are administered at or near the location of a clot to prevent further clot formation and/or mediate clot dissolution. In other aspects, RGT compositions are associated with an intra-arterial stint and thereby provide a localized anti-clotting effect at the location of the stint.

In certain aspects, compositions described herein are used in combination with additional therapeutic methods. Additional therapies are administered before, after or concurrently with RGT peptide compositions. For instance, in one aspect, RGT compositions are used in combination with surgical therapies, such as angioplasty, physical blood clot removal (or dissolution) or stint placement. In a specific example, a stint having a coating which comprises an RGT peptide composition is used to reduce the occurrence of restenosis. In other aspects, pharmaceutical agents are used in combination or in conjunction with RGT peptide compositions. Agents for use in combination therapies include but are not limited to agents that prevent platelet aggregation, anticoagulants and thrombolytic agents. For example, agents that reduce platelet aggregation include drugs such as clopidogrel (PLAVIX®), Ticlopidine (TICLID®), Cilostazol (PLETAL®), Abciximab (REOPRO®), Eptifibatide (INTEGRILIN®), Tirofiban (AGGRASTAT®), Defibrotide, Dipyridamole and aspirin. Some exemplary anticoagulants include, but are not limited to, warfarin, acenocoumarol, phenprocoumon, phenindione, heparin, fondaparinux, idraparinux, argatroban, lepirudin, bivalirudin or dabigatran. Thrombolytic agents for use in combination with RGT peptide compositions include, for example, streptokinase, tissue plasminogen activator (tPA) or urokinase. Thus, in some aspects, compositions comprising membrane permeant RGT peptides and at least a second therapeutic agent are provided.

In a further embodiment, the instant disclosure provides a composition comprising an RGT peptide having a lipid associated with or covalently attached thereto wherein the composition inhibits binding of Src to integrin in a platelet cell. In some aspects, RGT peptide compositions is further characterized as having a fatty acid, such as a saturated or unsaturated fatty acid (i.e., a cis- or trans-unsaturated fatty acid) associated with or covalently attached to the RGT peptide. Exemplary saturated fatty acids for use in RGT peptide compositions include but are not limited to butyric acid (butanoic acid, $CH_3(CH_2)_2COOH$); caproic acid (hexanoic acid, $CH_3(CH_2)_4COOH$); caprylic acid (octanoic acid; $CH_3(CH_2)_6COOH$); capric acid (decanoic acid, $CH_3(CH_2)_8COOH$); lauric acid (dodecanoic acid, $CH_3(CH_2)_{10}COOH$); myristic acid (tetradecanoic acid; $CH_3(CH_2)_{12}COOH$); palmitic acid (hexadecanoic acid, $CH_3(CH_2)_{14}COOH$); steric acid (octadecanoic acid, $CH_3(CH_2)_{16}COOH$); arachidic acid (eicosanoic acid, $CH_3(CH_2)_{18}COOH$); behenic acid (docosanoic acid, $CH_3(CH_2)_{20}COOH$) and lignoceric acid (tetracosanoic acid, $CH_3(CH_2)_{22}COOH$). For example, in one aspect, an RGT peptide composition comprises a myristic acid associated with or covalently attached to an RGT peptide. In another aspect, an RGT peptide composition comprises a molecule consisting of (or consisting essentially of) a lipid (e.g., a fatty acid such as myristic acid) associated with or covalently bound to a peptide consisting of (or consisting essentially of) the amino acid sequence RGT.

In still a further embodiment, the instant disclosure provides a method for identifying a compound that competes with an RGT peptide for Src binding comprising determining binding of a Src polypeptide to an RGT peptide in the presence or absence of a candidate compound. Such a method, in some cases, is used to identify additional agents for use in preventing platelet cell aggregation. Determining binding of a Src polypeptide to an RGT polypeptide, in some cases, comprises determining a Src kinase activity. Such methods, in certain aspects, employ any of the RGT peptide or RGT peptide compositions described herein. Furthermore, in other aspects, methods employ a Src polypeptide and/or an RGT peptide linked to a reporter such as and without limitation an enzyme, a radio isotope, a fluorescent moiety or a fluorescence quenching moiety. Additionally, in some aspects, a Src polypeptide or an RGT peptide is immobilized on a substrate. Methods are alternatively defined as cell-free methods (e.g., that employ recombinant or purified polypeptides); however, in some aspects a Src polypeptide is comprised in a cell, such as platelet cell.

Embodiments discussed in the context of a method and/or composition of the invention are in various aspects employed with respect to any other method or composition described herein. Thus, an embodiment pertaining to one method or composition is equally applied to other methods and compositions of the invention as well.

As used herein the specification, "a" or "an" means one or more. Thus, as used herein in the claim(s), when used in conjunction with the word "comprising", the words "a" or "an" mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" means at least a second or more.

Throughout this application, the term "about" is used to indicate that a value includes the inherent variation of error for the device, the method being employed to determine the value, or the variation that exists among the study subjects.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The following drawings are part of the present specification and are included to further demonstrate certain aspects of the present disclosure. The disclosure may be better understood by reference to the drawings in combination with the detailed description of specific embodiments presented herein.

FIG. 1A: Fluorescence histograms of platelets treated with FITC-conjugated myristoylated RGT peptide (FITC-myr-RGT, closed histogram) or with FITC-conjugated RGT peptide (FITC-RGT, open histogram) were analyzed by flow cytometry. FIG. 1B: Platelets were treated with FITC-myr-RGT peptide or FITC-RGT peptide and allowed to spread on immobilized fibrinogen for 30 min. The same microscopic fields were analyzed by differential interference contrast (DIC) microscopy as well as confocal fluorescence microscopy (fluorescence). Figure shows representative images made by an LSM510 confocal microscope (Zeiss) with a 63× plan-apochromat DIC oil immersion objective with Pascal software. FIG. 1C: Z-Stack scanning was performed on FITC-myr-RGT-treated platelets with intervals of 1.2 µm (from 1 to 4). The fluorescence density profiles are shown below each picture.

FIG. 2A: Platelets were added to microtiter wells precoated with fibrinogen and allowed to adhere for 30 min at 37° C. The phosphatase activity in supernatants (open columns) or in adherent platelets (close columns) was quantified by a PNPP assay. Data of three experiments (means and SD) were presented as the ratio of the phosphatase activity of platelet samples over blank. The asterisks indicate peptide concentration (* 62.5 µM;  125 µM; * 250 µM). FIG. 2B: Microphotographs of platelets adherent on fibrinogen and treated with DMSO (B1), myristic acid and RGT peptide at a concentration of 250 µM (B2), scrambled myr-GRT at 250 µM (B3), myr-RGT at 62.5 (B4), 125 (B5) and 250 µM (B6). DIC: differential interference contrast microscopy; IF: immunofluorescence assay with anti-integrin β3 antibody. FIG. 2C: Platelets were incubated in suspension with different treatments as indicated for 30 min at 37° C. The phosphatase activity in supernatants (open columns) or in remaining platelet suspensions (close columns) was quantified by a PNPP assay. Data are arranged as in FIG. 2A.

FIG. 3A-B: Effects of myr-RGT on fibrin clot retraction and platelet aggregation. FIG. 3A: Platelets were washed and resuspended in HEPES buffer containing 2 mg/ml of human fibrinogen (see "Experimental Procedures") and incubated with different peptides or their vehicles as indicated. Fibrin clot formation was initiated by adding 1 U/ml thrombin. Clot retraction was monitored over time and photographs of the clots were taken at different time points (lower panel). The asterisks indicate peptide concentration (* 62.5 µM;  125 µM; * 250 µM). The histograms of the clot size were generated from the photographs by calculating the ratio of the surface area of the retracted clot versus that of the initial clot. FIG. 3B: Aggregation of non-treated or peptide-treated platelets was induced in an aggregometer at 37° C. under constant stirring (1000 rpm) by ADP (2 µM), ristocetin (1.25 mg/ml) in PRP or by thrombin (0.1 U/ml) in washed platelets preincubated with (A) DMSO, (B) myristic acid and RGT peptide at a concentration of 250 µM, (C) scrambled myr-GRT at 250 µM, myr-RGT at concentrations of (D) 62.5, (E) 125 and (F) 250 µM respectively.

FIG. 4A: shows representative histograms. Fibrinogen bound to platelets treated with DMSO, myristic acid and RGT at 250 µM (M+RGT), scrambled myr-GRT at 250 µM (myr-GRT), myr-RGT at 250 µM (myr-RGT), or with RGDS peptide (1 mM). The background fibrinogen binding was assessed using platelets treated without ADP (Control). FIG. 4B: Statistical data were derived from quantitative results (means and SD) calculated from the ratios of mean fluorescence intensity (samples/control) of three separate experiments.

FIG. 5A-B: Effects of myr-RGT on platelet CD62P expression in the presence of a low dose of thrombin. The expression of CD62P on non-treated or peptide-treated platelets stimulated with 0.1 U/ml of thrombin was analyzed by flow cytometry using a FITC-labeled monoclonal anti-CD62P antibody (BECKMAN COULTER™). Data in FIG. 5A (means and SD) were derived from the ratio of the geometric mean fluorescence intensity measured for anti-CD62P antibody binding to thrombin-treated platelets, preincubated for 30 min with DMSO vehicle, nonmyristoylated RGT peptide (250 µM) plus myristic acid (M+RGT), scrambled myr-GRT (250 µM) or myr-RGT (250 µM), versus resting platelets (without thrombin treatment) and obtained from three separate experiments. FIG. 5B is a representative figure of CD62P expression in the presence of thrombin on platelets preincubated with DMSO (fine line), myr-RGT (normal line), or on resting platelets (in the absence of thrombin, thick line).

FIG. 7A: Platelets preincubated with 250 μM of myr-RGT or scrambled myr-GRT (indicated as *) were lysed with lysis buffer and the lysates of untreated or peptide-treated platelets were analyzed with an immunoprecipitation procedure as follows. The lysates were incubated with SZ21 antibody or nonspecific mouse IgG. After washing, the immune complexes were subjected to SDS-PAGE and probed by Western blotting using monoclonal antibodies to integrin αIIb (SZ22) or c-Src (327). Representative results out of 3 experiments are shown. FIG. 7B: Glutathione-Sepharose 4B beads coated with GST-wild type integrin β3 cytoplasmic tail fusion protein were incubated with purified His-SH3 in the presence of peptides as indicated overnight. After wash, protein complexes were subjected to Western blot analysis with anti-His or anti-GST antibodies. One to four asterisks respectively indicate peptide concentrations from 62.5 to 500 μM with duplicate increments. FIG. 7C: Increasing concentrations of purified GST-Src-SH3 or GST protein were added to the microtiter wells coated with RGT or GRT peptide (20 μg/ml). Binding of the purified proteins to the peptides was detected by incubation with mouse anti-GST antibody, followed by horseradish peroxidase-conjugated anti-mouse Ig antibody. Specific binding was normalized by subtracting the OD values of the blank wells from that of the sample wells. Results were presented as percentage of the maximal binding. Data were organized as binding of GST-Src-SH3 to RGT peptide (–●–), GST-Src-SH3 to GRT peptide (–◆–), GST protein to RGT peptide (–△–), GST protein to GRT peptide (–□–). FIG. 7D: Glutathione-Sepharose 4B beads coated with GST-integrin β3 cytoplasmic tail fusion proteins were incubated with platelet lysates overnight at 4° C. Immobilized protein complexes were further incubated with peptides as indicated, before lysed by SDS sample buffer. Talin was detected with the monoclonal antibody 8d4. Anti-GST antibody binding was used to verify the loading of the β3 cytoplasmic tail fusion proteins. The increased electrophoretic mobility of GST-β3-741 documents the 21 residue truncation of this fusion protein.

DETAILED DESCRIPTION

Figure 1A:
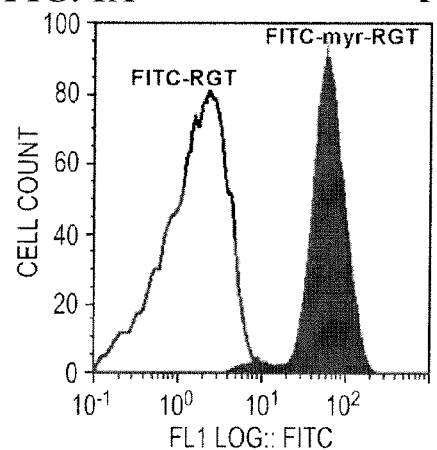
FIG. 1A-C: Intraplatelet localization of the membrane-permeable peptides. Platelets incubated with FITC-conjugated peptides (250 µM) for 30 min and analyzed by flow cytometry and fluorescence microscopy.

Integrin αIIbβ3 is an ideal antithrombotic target as its activation is the final common pathway mediating platelet aggregation in response to many different agonists. However, existing integrin αIIbβ3 receptor antagonists that block ligand binding have to be used at a defined dose that has a significant inhibition of thrombosis without undue bleeding (Phillips et al., 2005). Also, some ligand-mimetic αIIbβ3 antagonists have been reported to cause conformational changes of αIIbβ3 and elicit outside-in signaling (Bassler et al. 2007). In contrast, RGT peptide compositions described here caused a selective inhibition of outside-in signaling-related platelet functions. Thus, the compositions disclosed here provide novel anti-platelet aggregation agents with the potential for improved efficacy and reduced side-effects (e.g., bleeding) profiles. Thus, therapies which employ these new compositions could significantly improve the treatment of blood clot and ischemia related diseases.

Aberrant regulation of platelet aggregation is implicated in a variety of clinically important disease conditions. Aberrant aggregation of platelet cells can disrupt normal blood flow and result in local ischemia and tissue death. Ischemic events resulting from platelet aggregation (clotting) such as myocardial infarction and thrombic stroke account for a significant number of deaths and hospitalizations each year. Therapy and prophylaxis for such conditions have been developed, but there remains a need for additional, effective therapeutic and prophylactic regimens. However, because the cell signaling mechanisms that underlie platelet aggregation are not fully understood, specific therapeutic regimens could not, previously, be designed to address this need. The instant disclosure concerns modulation of integrin β3 signaling in platelet cells as a route for altering platelet aggregation. In particular, by displacing Src from integrin β3, platelet aggregation can be reduced. It is demonstrated herein that cell-permeating peptides comprising the amino acid sequence RGT displace Src from integrin β3 in platelet cells and prevent phosphorylation of integrin β3 thereby reducing platelet aggregation.

Studies detailed herein demonstrate the role of the RGT peptide sequence in integrin β3-Src signaling and on platelet aggregation. Cell permeant RGT peptide (exemplified by myristoylated RGT (myr-RGT) peptide) was readily internalized into human platelets and it selectively interfered with integrin outside-in signaling in a dose-dependent manner. The RGT peptide composition exhibited inhibitory effects on platelet spreading, secretion, as well as clot retraction mediated by washed human platelets. Inhibitory effect were only observed in platelets treated with myr-RGT while a scrambled myristoylated peptide or non-myristoylated RGT peptide did not exhibit activity. Also, myr-RGT did not cause platelet lysis as demonstrated by data with platelets in suspension or following adhesion. Importantly, RGT compositions abolished β3 interaction with the Src SH3 domain and inhibited β3 cytoplasmic tyrosine phosphorylation. Moreover, in primary platelet-rich blood preparations, myr-RGT was able to reduce the size of blood clots formed upon stimulation with thrombin. In view of these studies cell permeant RGT may be employed as a new class of antithrombotic agent.

I. CELL PERMEANT COMPOSITION

As described above in certain aspects the instant disclosure concerns a cell permeant composition comprising an RGT peptide. In particular a cell permeant composition has the ability to pass though or be transported across the membrane of cells. Various methods have been reported in the literature for peptide delivery into, for example, platelets. Platelet membrane becomes permeable to peptides by streptolysin O treatment (Hers et al., 2000 and Litjens et al., 2003[1]) or electroporation (Litjens et al., 2003[2]). In addition, chemical modifications such as myristoylation or palmitoylation (Tsuboi, 2002; Martin et al., 2003; Dai et al., 2005; Larkin et al., 2004; Liu et al., 2005; Vinogradova et al., 2000; Stephens et al., 1998; Ginsberg et al., 1985) or attachment of or association with a hydrophobic sequence (Liu et al., 1996 and Wang et al., 2003) render the peptides membrane permeable. However, some of these methods have been shown to interfere with normal platelet functions, in particular streptolysin O-treated platelets exhibited reduced adhesion (Hers et al., 2000; Litjens et al., 2003[2]).

In some aspects, RGT peptides are covalently linked to or associated with a fatty acid, or in certain aspects a saturated fatty acid such as butyric acid (butanoic acid, $CH_3(CH_2)_2COOH$); caproic acid (hexanoic acid, $CH_3(CH_2)_4COOH$); caprylic acid (octanoic acid; $CH_3(CH_2)_6COOH$); capric acid (decanoic acid, $CH_3(CH_2)_8COOH$); lauric acid (dodecanoic acid, $CH_3(CH_2)_{10}COOH$); myristic acid (tetradecanoic acid; $CH_3(CH_2)_{12}COOH$); palmitic acid (hexadecanoic acid, $CH_3(CH_2)_{14}COOH$); steric acid (octadecanoic acid, $CH_3(CH_2)_{16}COOH$); arachidic acid (eicosanoic acid, $CH_3(CH_2)_{18}COOH$); behenic acid (docosanoic acid, $CH_3(CH_2)_{20}COOH$) or lignoceric acid (tetracosanoic acid, $CH_3(CH_2)_{22}COOH$). RGT peptides may also be covalently linked to or associated with an unsaturated fatty acids, such as a cis- or trans-unsaturated fatty acid. Some exemplary unsaturated fatty acids include but are not limited to myristoleic acid ($CH_3(CH_2)_3CH=CH(CH_2)_7COOH$), palmitoleic acid $CH_3(CH_2)_5CH=CH(CH_2)_7COOH$, oleic acid ($CH_3(CH_2)_7CH=CH(CH_2)_7COOH$), linoleic acid ($CH_3(CH_2)_4CH=CHCH_2CH=CH(CH_2)_7COOH$), α-linolenic acid ($CH_3CH_2CH=CHCH_2CH=CHCH_2CH=CH(CH_2)_7COOH$), arachidonic acid ($CH_3(CH_2)_4CH=CHCH_2CH=CHCH_2CH=CH(CH_2)_3COOH$), eicosapentaenoic acid ($CH_3CH_2CH=CHCH_2CH=CHCH_2CH=CHCH_2CH=CH(CH_2)_3COOH$), erucic acid ($CH_3(CH_2)_7CH=CH(CH_2)_{11}COOH$) and docosahexaenoic acid ($CH_3CH_2CH=CHCH_2CH=CHCH_2CH=CHCH_2CH=CHCH_2CH=CH(CH_2)_2COOH$).

II. PEPTIDE PRODUCTION AND PURIFICATION

In some embodiments of the invention, the source of the RGT peptide is from cells that express the peptide. For instance, in one aspect, cells are transformed with a nucleic acid vector that expresses an RGT peptide or a precursor thereof. These cells, in various aspects, comprise mammalian cells, bacterial cells, yeast cells, insect cells, whole organisms, or other cells that are a useful source recombinant protein. The RGT peptide or RGT peptide precursor is, optionally, purified from the cells by methods known to those of skill in the art.

Thus, in certain embodiments, the invention concerns isolated DNA segments and/or recombinant vectors that encode an RGT peptide and control sequences that direct peptide expression in bacterial, mammalian or insect cells. It will also be understood that RGT amino acid and/or nucleic acid sequences optionally include additional residues, such as additional N- and/or C-terminal amino acids and/or 5' and/or 3' sequences.

In some cases it is desirable that the recombinant RGT coding sequence be fused with additional amino acid sequence. For example, in one aspect, expressed protein is tagged for purification. Some possible fusion proteins that are expressed include histadine tags, Glutathione S-transferase (GST), Maltose binding protein (MBP), Flag and myc tagged RGT. These additional sequences are used to aid in purification of the recombinant protein, and in some cases are removed by protease cleavage. For example, in one aspect, a coding sequence for a specific protease cleavage site is inserted between the RGT coding sequence and the purification tag coding sequence. One example for such a sequence is the cleavage site for thrombin. Thus fusion proteins are cleaved with the protease to free the RGT peptide or peptide derivative from the purification tag. In further embodiments, recombinant RGT protein or RGT precursors further comprise a secretion signal that allows the recombinant protein to be secreted from expressing cells. Thus in some embodiments, RGT peptide or RGT peptide precursors is purified from the media of expressing cells.

Any of the wide variety of vectors known to those of skill in the art are used to express RGT peptides. For example, in certain aspects, plasmids, phagmids or viral vectors are used. In certain embodiments vectors for expression of RGT peptides or a variant thereof may comprise a promoter sequence. In some applications the promoter sequence may be a regulated or inducible promoter. In applications in which eukaryotic expression vectors are used the vector optionally comprises a poly-adenylation signal sequence. It is well understood to these of skill in the art that these vectors are introduced in to cells by a variety of methods including but not limited to, transfection (e.g, by liposome, calcium phosphate, electroporation, particle bombardment, etc.), transformation, and viral transduction. In some additional embodiments, the expression vectors of the invention is stably maintained in cells. For example the expression region is, in some cases, integrated into the genomic DNA of the expressing cell. Alternatively or additionally, the expression vector further comprises one or more drug resistance marker(s) that allow selection of cells that express the vector by treatment of a cell population with said drug.

It is further contemplated that an RGT peptide is in some aspects chemically synthesized. Methods for chemical synthesis of peptide sequences are well known in the art and commercial services for high quality peptide synthesis are also readily available.

III. PHARMACEUTICAL COMPOSITIONS

Pharmaceutical compositions comprising cell permeant RGT peptide are also contemplated. The phrases "pharmaceutical or pharmacologically acceptable" refers to molecular entities and compositions that do not produce an adverse, allergic or other untoward reaction when administered to an animal, such as, for example, a human. The preparation of a pharmaceutical composition including a RGT peptide will be known to those of skill in the art in light of the present disclosure, as exemplified by Remington's Pharmaceutical Sciences, 18th Ed. Mack Printing Company, 1990. Moreover, for animal (e.g., human) administration, it will be understood that preparations should meet sterility, pyrogenicity, general safety and purity standards as required by FDA Office of Biological Standards.

"Therapeutically effective amounts" are those amounts effective to produce beneficial results in the recipient animal or patient. Such amounts are initially determined by reviewing the published literature, by conducting in vitro tests or by conducting metabolic studies in healthy experimental animals. Before use in a clinical setting, it is often beneficial to conduct confirmatory studies in an animal model, preferably a widely accepted animal model of the particular disease to be treated. Animal models for use in certain embodiments are, without limitation, rodent models, which are economical to use and, particularly, are widely accepted as predictive of clinical value.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990).

In certain embodiments compositions comprising an RGT peptide are delivered as a liposomal composition. For example, the RGT peptide may be presented on the surface of (membrane associated) or be encapsulated within a liposome. As used herein the term "liposome" refers to a lipid composition comprising one or more concentric layers of lipid molecules. Liposomes include those which are cationic, anionic or neutral, and in some cases liposomes are stabilized by the addition of protein and/or additional lipids or cholesterol. Liposomes are prepared in accordance with known laboratory procedures such as those disclosed in Bangham et al. (1965), Gregoriadis (1979), Deamer and Uster (1983), or Szoka and Papahadjopoulos (1978), the contents of which are each incorporated herein by reference.

The actual dosage amount of a composition of the present invention administered to an animal patient is determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 50%, 25%, 10%, 5%, 3%, 1%, 0.5%, 0.1% or 0.05% of an active compound. In other embodiments, the an active compound may comprise between about 0.1%, 0.5%, 1%, 2%, or 5% to about 10%, 15%, 25%, 50% or 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition optionally comprises various antioxidants to retard oxidation of one or more component. Additionally, the prevention of the action of microorganisms is brought about by preservatives such as various antibacterial and antifungal agents, including but not limited to parabens (e.g., methylparabens, propylparabens), chlorobutanol, phenol, sorbic acid, thimerosal or combinations thereof.

The compositions of the present invention optionally comprise different types of carriers depending on whether it is to be administered in solid, liquid or aerosol form, and whether it need to be sterile for such routes of administration as injection.

The compositions are formulated into a composition for example in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups are in one aspect derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier includes a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity is maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, the composition includes isotonic agents, such as, for example, sugars, sodium chloride or combinations thereof.

In other embodiments, use eye drops, nasal solutions or sprays, aerosols or inhalants are contemplated in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments, the aqueous nasal solutions are isotonic or slightly buffered to maintain a pH of about 5.5 to about 6.5. In addition, antimicrobial preservatives, similar to those used in ophthalmic preparations, drugs, or appropriate drug stabilizers, if required, are included in the formulation. For example, various commercial nasal preparations are known and include drugs such as antibiotics or antihistamines.

In certain embodiments, the compositions are prepared for administration by such routes as oral ingestion. In these embodiments, the solid composition comprises, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions are often incorporated directly with the food of the diet. Carriers for oral administration comprise for example inert diluents, assimilable edible carriers or combinations thereof. In other aspects of the invention, the oral composition is prepared as a syrup or elixir. A syrup or elixir, in certain aspects comprises, for example, at least one active agent, a sweetening agent, a preservative, a flavoring agent, a dye, a preservative, or combinations thereof.

In certain embodiments, an oral composition comprises one or more binders, excipients, disintegration agents, lubricants, flavoring agents, and combinations thereof. In certain embodiments, a composition comprises one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof a disintegrating agent, such as, for example, corn starch, potato starch, alginic acid or combinations thereof a lubricant, such as, for example, magnesium stearate; a sweetening agent, such as, for example, sucrose, lactose, saccharin or combinations thereof a flavoring agent, such as, for example peppermint, oil of wintergreen, cherry flavoring, orange flavoring, etc.; or combinations thereof the foregoing. When the dosage unit form is a capsule, it optionally contains, in addition to materials of the above type, carriers such as a liquid carrier. Various other materials are contemplated as coatings or to otherwise modify the physical form of the dosage unit. For instance, tablets, pills, or capsules are often coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories are formed from mixtures containing, for example, the active ingredient in the range of about 0.5% to about 10%, and preferably about 1% to about 2%.

Sterile injectable solutions are prepared by incorporating the active compound(s) in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, methods of preparation include vacuum-drying or freeze-drying techniques which yield a powder of the active ingredient plus any additional desired ingredient from a previously sterile-filtered liquid medium thereof. The liquid medium is generally suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition is generally stable under the conditions of manufacture and storage, and preserved against the contaminating action of microorganisms, such as bacteria and fungi. It will be appreciated that exotoxin contamination are kept minimally at a safe level, for example, in one aspect less that 0.5 ng/mg protein.

IV. COMBINATION THERAPIES

In order to increase the effectiveness of a treatment with the compositions of the present invention, it is in one aspect desirable to combine these compositions with other therapies effective in the treatment of specific diseases or conditions.

In some cases, the compositions of the present invention precede or follow the other agent treatment by intervals ranging from minutes to weeks. It is contemplated that one administers both modalities within about 12-24 h of each other or within about 6-12 h of each other. In some situations, it is desirable to extend the time period for treatment significantly, where several days (2, 3, 4, 5, 6 or 7) to several weeks (1, 2, 3, 4, 5, 6, 7 or 8) lapse between the respective administrations.

In certain specific instances RGT compositions are administered in combination with a second agent to prevent or treat an ischemic event or to mediate shrinkage or dissolution of a blood clot. For examples, agents that are useful in combination therapies include, but are not limited to, antiplatelet agents (i.e., agents that reduce platelet aggregation), anticoagulant agents or thrombolytic agents.

Antiplatelet Agents and Anticoagulants

Antiplatelet agents can reduce or prevent platelet cell aggregation and are often used to reduce the occurrence of primary or secondary ischemic events that may result from clot formation. Exemplary antiplatelet agents include cyclooxygenase inhibitors such as aspirin, Adenosine diphosphate (ADP) receptor inhibitors, such as Clopidogrel (PLAVIX®) or Ticlopidine (TICLID®), Phosphodiesterase inhibitors (e.g., Cilostazol (PLETAL®)), Glycoprotein IIB/IIIA inhibitors, such as Abciximab (REOPRO®), Eptifibatide (INTEGRILIN®), Tirofiban (AGGRASTAT®) or Defibrotide, and adenosine reuptake inhibitors (e.g., Dipyridamole (PERSANTINE®)). Clopidogrel, for instance, is disclosed in U.S. Pat. Nos. 4,529,596, 6,258,961, 5,036,156, 6,080,875 and 6,180,793, all of which are incorporated herein by reference for their disclosure and preparation of clopidogrel. Methods for using clopidogrel for preventing secondary ischemic events are described in U.S. Pat. No. 5,576,328, incorporated herein by reference.

Another related group of agents often used to prevent ischemic events or treat blood clot disorders are anticoagulant agents. For example, agents that antagonize the effects of vitamin K, such as coumarin derivatives (e.g., warfarin, acenocoumarol or phenprocoumon) or phenindione can be used as anticoagulants. Heparin derivatives, such as low molecular weight heparin, and small molecules fondaparinux and idraparinux are also common anticoagulants that may be employed in combination therapies. Another common group of anticoagulant agents include direct thrombin inhibitors such as argatroban, lepirudin, bivalirudin and dabigatran.

Thrombolytic Agents

RGT peptide compositions are optionally used in combination or in conjunction with thrombolytic agents that breakdown blood clots. One of the most common thrombolytic agents is tissue plasminogen activator (T-Pa), a serine protease available in a number of formulations. For example, reteplase (Retavase) is a recombinant non-glycosylated T-Pa. Likewise, tenecteplase T-Pa is a recombinant T-Pa produced in a mammalian cell line which comprises glycosylation. Additional agents which operate via a similar mechanism as T-Pa include anistreplase, streptokinase, urokinase and brinase.

V. EXAMPLES

Example 1

Membrane Permeability of the Myristoylated RGT Peptide

Synthetic peptides were obtained from GL Biochem, and myristoylated peptides were synthesized with myristoylate covalently linked to their N-terminal amino acid. The peptides were purified by reverse phase-high performance liquid chromatography using a C-18 column with purity higher than 98%. The expected mass spectra were verified by electrospray ion-trap mass spectrometry.

Platelets were prepared as described in Li et al. (2001). Briefly, whole blood was drawn by venipuncture from healthy volunteers with informed consent, and collected into 1/10 volume of 3.8% (w/v) trisodium citrate. The blood was centrifuged at 300×g for 20 min at 22° C. and platelet-rich plasma (PRP) was collected. Platelet counts in PRP were adjusted to $3 \times 10^8$/ml by adding platelet-poor plasma (PPP). For preparation of washed platelets, blood was anticoagulated by 1/7 volume of ACD (85 mM trisodium citrate, 83 mM dextrose and 21 mM citric acid). The RPR was recentrifuged at 1500×g for 20 min. Pelleted platelets were washed twice with CGS (120 mM NaCl, 13 mM trisodium citrate, 30 mM glucose, pH 6.5), and were finally resuspended at a concentration of $3 \times 10^8$/ml in Tyrode's buffer (137 mM NaCl, 2 mM KCl, 12 mM $NaHCO_3$, 0.3 mM $NaH_2PO_4$, 5.5 mM glucose, 5 mM HEPES, 0.1% BSA, pH7.4) containing extemporaneously added 1 mM CaCl$_2$ and MgCl$_2$. The platelet suspension was allowed to stand at room temperature for 60 min before use.

Figure 1B:
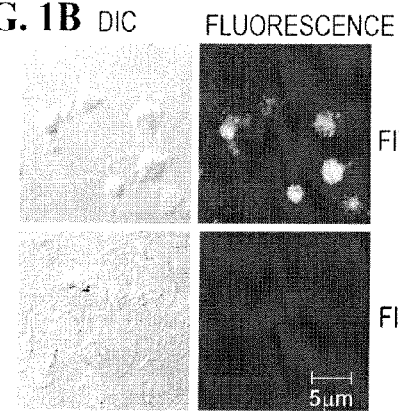
Figure 1C:
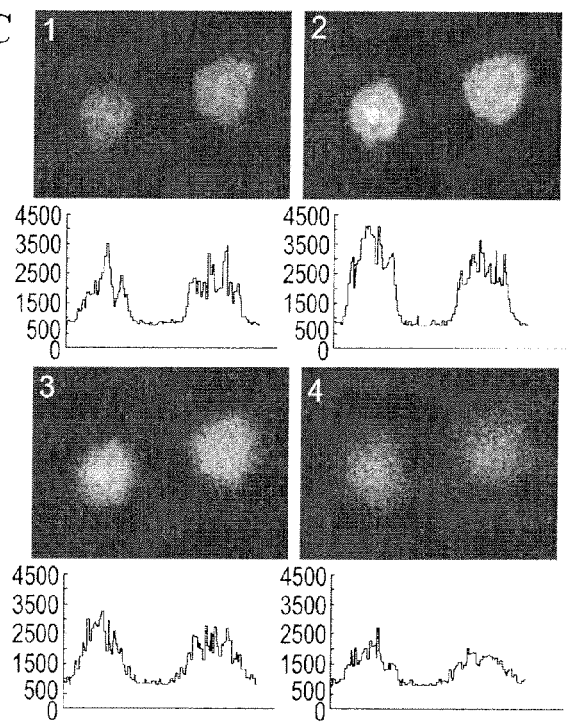

To test peptides for their ability to penetrate the membrane of living cells, myristoylated and nonmyristoylated RGT peptides were labeled with FITC (Sigma) as described by Tsuboi (2002) and assayed by flow cytometry and confocal microscopy. Flow cytometry analysis showed that platelets incubated with FITC-labeled myr-RGT became fluorescent (FIG. 1A). In confocal microscopy analysis, all platelets treated with myr-RGT exhibited a strong overall fluorescence (FIG. 1B). In contrast, platelets treated with the non-myristoylated peptide, while visible with DIC imaging, were fluorescently negative (FIG. 1B). Z-position sectional analysis of FITC-myr-RGT-treated platelets continued the intracellular localization of the peptide (FIG. 1C).

Example 2

Inhibition of Platelet Stable Adhesion and Spreading on Immobilized Fibrinogen by myr-RGT An important function of integrin αIIbβ3 outside-in signaling is to mediate stable platelet adhesion and spreading on immobilized ligands. Platelets with impaired outside-in signaling are hence less resistant to detachment in adhesion assays. For quantitative analysis of the effect of the RGT peptide on platelet adhesion, we used a phosphatase assay. The platelet adhesion assay was performed as previously described with minor modifications (Xi et al., 2003). Briefly, 96-well microtiter plates were coated overnight at 4° C. with 0.05 ml of either human fibrinogen (20 mg/ml) or BSA (10 mg/ml) in 0.1 M NaHCO$_3$, pH 8.3. The wells were blocked for 2 h at room temperature with 20 mg/ml BSA. Washed platelets in Tyrode's buffer at a concentration of 2×10$^8$/ml were incubated with peptides at indicated concentrations for 30 minutes at 37° C. Platelets (100 µl) were added to the pre-coated wells in triplicate and incubated at 37° C. for 60 min. Nonadherent platelets were removed by three vigorous washes with phosphate-buffered saline (PBS), and adherent platelets were quantified by a phosphatase assay. In addition, to monitor peptide-dependent platelet lysis, the platelet phosphatase activity was separately measured in the supernatant of the platelets in suspension or following their adhesion to fibrinogen by mixing with PNPP substrate solution (100 mM sodium acetate, 1% Triton X-100, 3 mg/ml p-nitrophenyl phosphate) for 60 min at 37° C. The enzyme reaction was stopped with 0.1 M NaOH and the optical density was measured at 405 nm with a microplate reader.

Figure 2A:
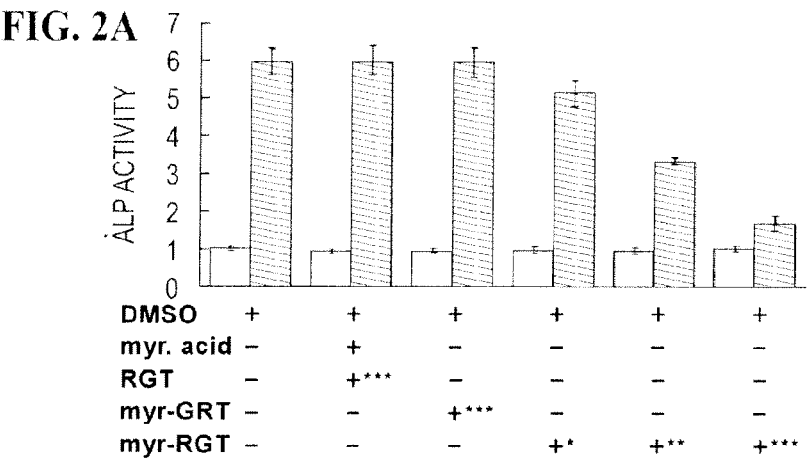
FIG. 2A-C: Quantitative analysis of the effect of myristoylated RGT peptide on platelet stable adhesion and spreading on immobilized fibrinogen.
Figure 2B:
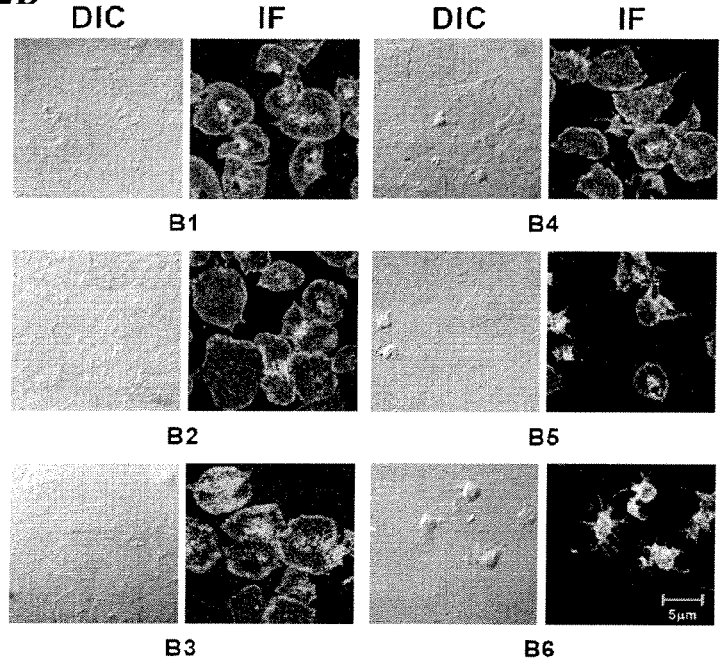
Figure 2C:
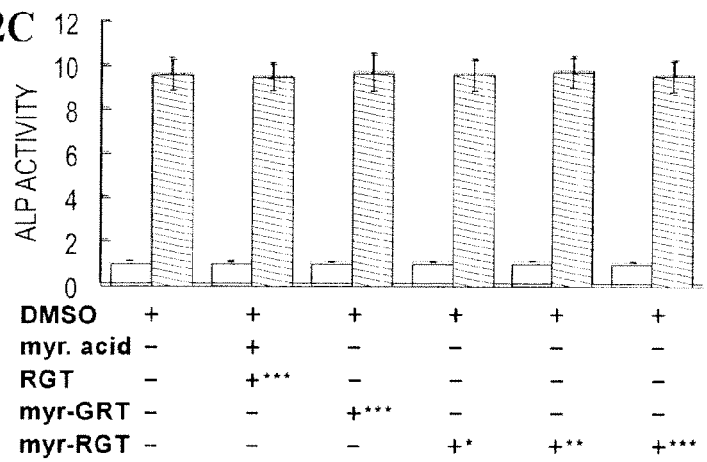

As shown in FIG. 2A, myr-RGT dose-dependently inhibited platelet stable adhesion on immobilized fibrinogen, while control peptides, or myristic acid or the vehicle DMSO had no significant inhibitory effect. A 50% inhibition of platelet adhesion was obtained with a 125 µM concentration of myr-RGT, while maximal inhibition was achieved at 250 µM. Parallel analysis of DIC images revealed a dose-dependent inhibition of platelet spreading on immobilized fibrinogen by myr-RGT (FIG. 2B). In addition, we measured the phosphatase activity in the supernatant of adherent platelets or of platelets in suspension. No difference was observed between myr-RGT-treated and nontreated platelets either following adhesion (FIG. 2A) or in suspension (FIG. 2C), indicating that myr-RGT did not induce platelet lysis. With or without myr-RGT in the adhesion buffer did not significantly alter the adhesion of myr-RGT-pretreated platelets.

Example 3

Effect of myr-RGT on Platelet-Mediated Fibrin Clot Retraction

Platelet clot retraction is an essential step in platelet thrombus consolidation and is initiated following platelet activation as a late consequence of integrin outside-in signaling. It also relies on an efficient extracellular fibrinogen-integrin interaction as well as a stable integrin-cytoskeletal association. In order to investigate whether myr-RGT has an effect on this important platelet function, a plasma-free platelet clot retraction assay was performed using washed platelets pretreated with different peptides (see, e.g., Osdoit et al., 2001 and Podolnikova et al., 2003). Clot retraction was performed as described previously. 24; 25 In brief, washed platelets (3×10$^8$/ml) in resuspension buffer (10 mM HEPES, pH7.4, 140 mM NaCl, 3 mM KCl, 0.5 mM MgCl$_2$, 5 mM NaHCO$_3$, 10 mM glucose) with extemporaneously added CaCl$_2$ (1 mM) were incubated with the peptides for 30 min at 37° C. Fibrinogen was then added to a final concentration of 2 mg/ml, and the platelets were dispensed in 0.25 ml aliquots into siliconized glass tubes. Clot retraction was initiated by the addition of human α-thrombin to a final concentration of 1 U/ml and allowed to proceed at 37° C. Clot retraction was monitored over a 90 min time period by taking photographs at indicated time points using a digital camera. Clot retraction was quantified on the photographs by measuring the clot surface area with the NIH Image 1.67e software, and the data were processed using Excel 4.0. Results were expressed as percentage of retraction (%=area t/area t0×100%).

As shown in FIG. 3A, at 30, 60, 90 minutes, the fibrin clots in the control tubes underwent a time-dependent retraction that started at 30 min and was complete at 90 min. For quantitative analyses of the effects of the different peptides, clot retraction was measured at 60 min. The presence of myr-RGT at 62.5 µM resulted in a weak, but recognizable, inhibition of clot retraction. When the concentration of the peptide was increased to 125 µM the inhibition reached a full scale in terms of clot size, while the clot retraction did occur under this condition to a subtle extent judging from the change of clot density. A complete inhibition was achieved with the addition of 250 µM of myr-RGT, a result comparable to that seen in the presence of 1 mM RGDS known to inhibit clot retraction by preventing the extracellular fibrinogen-integrin αIIbβ3 interaction. These results demonstrated that myr-RGT dose-dependently inhibited clot retraction in an experimental system with purified fibrinogen and washed platelets.

Example 4

Modulation of Platelet Aggregation by myr-RGT

Full scale platelet aggregation in response to low concentrations of agonists comprises the first wave of reversible aggregation that is mediated by inside-out signaling and ligand binding to αIIbβ3, and the second wave of irreversible aggregation that requires αIIbβ3-dependent outside-in signaling, and consequent aggregation-dependent platelet granule secretion (Shattil et al., 1998). To determine whether myr-RGT interferes with integrin signaling during platelet activation, its effect on platelet aggregation induced by ADP and ristocetin were investigated. Platelet aggregation was performed as previously described in Li et al., (2001). PRP at a platelet concentration of 3×10$^8$/ml was pre-incubated in glass vials for 10 min at 37° C. in the presence or absence of peptides and stimulated with ADP (2 µM) or ristocetin (1.25 mg/ml) at 37° C. under constant stirring at 1000 rpm. Thrombin-induced platelet aggregation was performed with washed platelets at a concentration of $2.5 \times 10^8$/ml in Tyrode's buffer and by the addition of thrombin (0.1 U/ml). Platelet aggregation was monitored in a lumi-aggregometer (Chrono-Log). It is notable, as shown in FIG. 3B, that in the presence of myr-RGT, the primary wave of platelet aggregation was intact. In contrast, the secondary wave of platelet aggregation was significantly affected at a peptide concentration of 125 µM and was completely abrogated at higher concentrations (250 µM).

The effect of myr-RGT on washed platelet aggregation induced by low-dose thrombin was also studied. In the presence of myr-RGT at 62.5 µM, 125 µM, 250 µM, the aggregation in response to thrombin was reduced to 60%, 46%, 39% of controls, respectively. In control experiments, myristic acid plus equal concentrations of nonmyristoylated RGT peptide did not inhibit aggregation. Furthermore, the scrambled peptide, myr-GRT, failed to significantly affect platelet aggregation even at a high concentration (250 µM).

Example 5

Effect of myr-RGT on Soluble Fibrinogen Binding

Figure 4A:
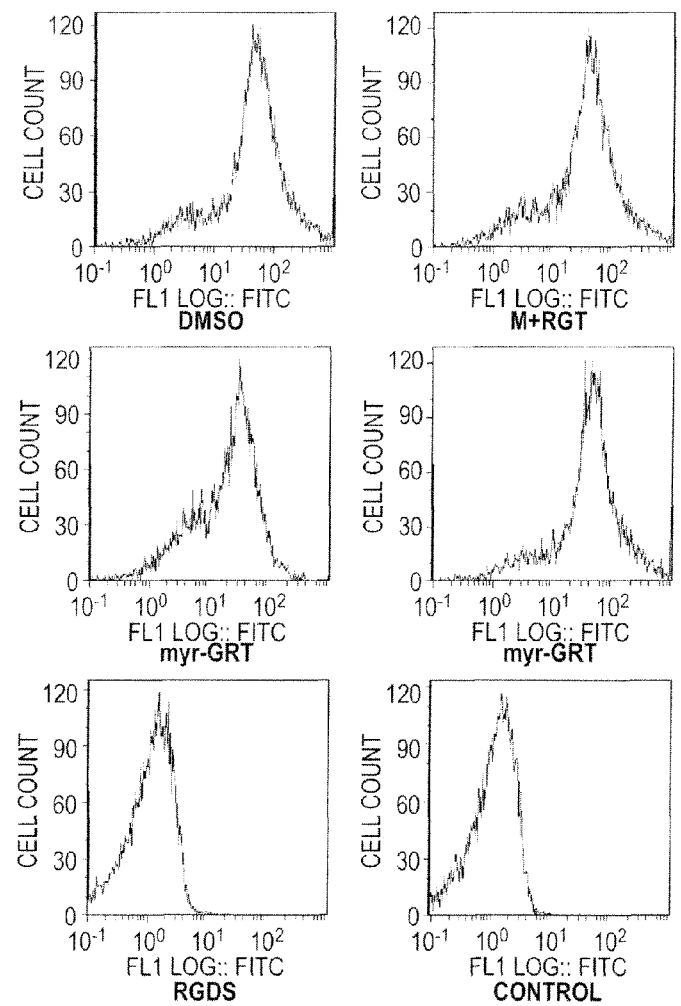
FIG. 4A-B: Effect of myr-RGT on soluble fibrinogen binding to platelets. Platelets were preincubated with different peptides or their vehicle and binding of Alexa Flour 488-conjugated fibrinogen (100 µg/ml) to platelets was measured by flow cytometry following the addition of 20 µM of ADP and the incubation for 30 min at room temperature.
Figure 4B:
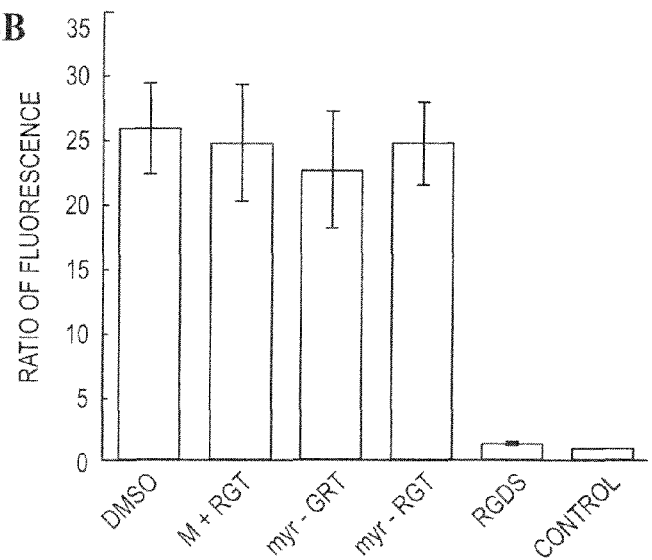

To investigate whether myr-RGT affects inside-out integrin signaling, its effect on soluble fibrinogen binding to integrin αIIbβ3 was investigated. Washed platelets were suspended in Tyrode's buffer at $3 \times 10^8$/ml and fibrinogen binding was measured (see, e.g., Angelillo-Scherrer et al., 2005 and Prevost et al., 2004). Peptides were added to the platelets up to 250 µM for a 30-min incubation at 37° C. Then the suspension was incubated with or without ADP (20 µM) in the presence of fluorescently (ALEXA FLOUR™ 488)-labeled fibrinogen (100 µg/ml) for 30 min at room temperature in dark. Platelet-bound fluorescence was analyzed on an EPICS XL flow cytometer (Beckman Coulter). Samples treated with 1 mM of RGDS served as control. Interestingly, as shown in FIG. 4, when stimulated by ADP, platelets preincubated with myr-RGT demonstrated an equivalent ability to bind soluble fluorescently (ALEXA FLOUR™ 488)-conjugated fibrinogen as those preincubated with the control scrambled peptide or the nonmyristoylated RGT peptide at concentrations up to 250 µM. In contrast, soluble fibrinogen binding to ADP-stimulated platelets was almost completely inhibited by 1 mM integrin inhibitor RGDS (FIG. 4B). These data provide evidence that inside-out signaling and thus the ligand binding to the integrin αIIbβ3 was not affected by the intracellular presence of myr-RGT.

Example 6

P-Selectin Expression on Platelets Treated with myr-RGT

The selective inhibition of secondary wave of platelet aggregation by myr-RGT suggests that myr-RGT interferes with aggregation-dependent platelet granule secretion, an event known to require integrin outside-in signaling. To test this hypothesis, the effect of myr-RGT on P-selectin surface exposure as a marker of integrin-dependent α-granule release and ATP release as a marker of dense granule secretion were determined. P-selectin expression was measured with a protocol using fluorescein-labeled anti-CD62P antibody (see, e.g., Li et al., 2004). Washed platelets in Tyrode's buffer at a concentration of $2 \times 10^8$/ml were pre-incubated with peptides (250 µM) at 37° C. for 30 min. The platelets were then stimulated for 3 min with or without thrombin (0.1 U/ml) at 37° C. and immediately fixed with 1% paraformaldehyde. The fixed platelets were labeled with a FITC-CD62P antibody at concentrations recommended by the manufacturers. A same conjugated non-specific mouse isotype IgG was used as negative control. P-selectin surface expression was analyzed by flow cytometry.

Results of these studies demonstrated that myr-RGT significantly inhibited P-selectin exposure on platelets (FIG. 5) or ATP release induced by a low concentration of thrombin. An inhibition of about 80% compared to the control was observed at a peptide concentration of 250 µM. In contrast, no significant effect was observed with control peptides used at the highest concentration of 250 µM. Similarly, myr-RGT also significantly inhibited dense granule secretion. These results are in agreement with the inhibitory effects of myr-RGT on the secondary wave platelet aggregation, platelet spreading and clot retraction, indicating that the functional outcome of integrin outside-in signaling was inhibited by myr-RGT.

Example 7

Regulation of Integrin β3 Cytoplasmic Tyrosine Phosphorylation by myr-RGT

Figure 6:
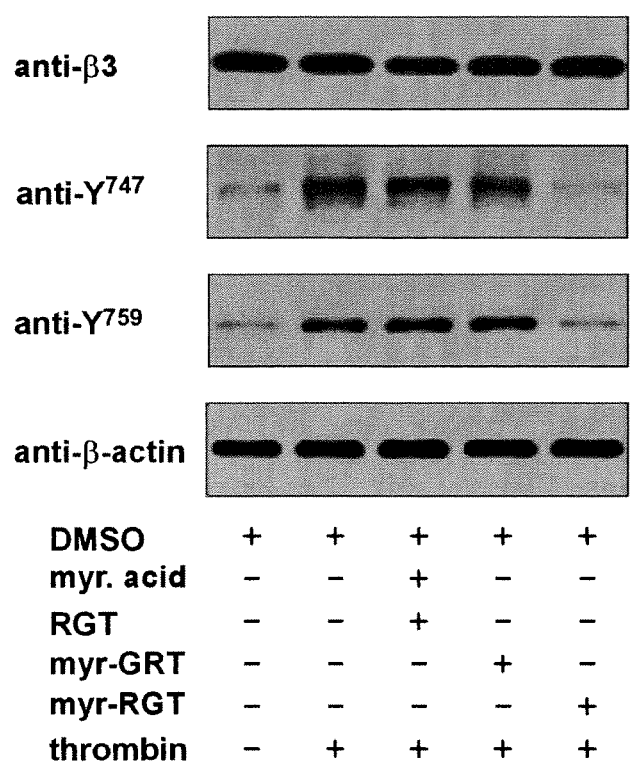
FIG. 6: Effect of myr-RGT on thrombin-induced phosphorylation of integrin β3 cytoplasmic $Y^{747}$ and $Y^{759}$. Washed platelets were preincubated for 30 min with 250 µM of the different peptides as indicated. Thrombin (0.05 U/ml) was added to induce platelet aggregation with stirring at 1000 rpm for 1 min. The platelets were then lysed in SDS-PAGE sample buffer and analyzed by Western blotting using monoclonal antibodies directed against the integrin β3 subunit extracellular domain (SZ21), β-actin, and polyclonal antibodies specific for the β3 integrin cytoplasmic sequences containing phosphorylated $Y^{747}$ or $Y^{759}$ residue respectively.

Previous studies have established that the post-occupancy events of integrin αIIbβ3 are closely related to the phosphorylation of two tyrosine residues present within the β3 cytoplasmic tail (Law et al., 1999). Because Src interacts with β3 cytoplasmic domain at the C-terminal RGT site and myr-RGT inhibited platelet function mediated by outside-in signaling, the effect of myr-RGT may be associated with its inhibition of Src-mediated phosphorylation of β3 cytoplasmic domain. To test this hypothesis, β3 tyrosine phosphorylation at Y747 and Y759 was determined by Western blotting using antibodies specific for integrin β3 cytoplasmic sequences containing phosphotyrosine residues at position 747 or 759 (see, e.g., Xi et al., 2006 and Law et al., 1996). Washed platelets ($1 \times 10^9$/ml in Tyrode's buffer) were pre-incubated with peptides at 250 µM for 30 min and were stimulated by α-thrombin (0.05 U/ml) with stirring at 1000 rpm for 1 min. The reactions were terminated by the addition of SDS-PAGE sample buffer containing 1 mM EDTA, 2 mM sodium vanadate, 1 mM PMSF, complete protease inhibitor cocktail (Roche Molecular Biochemicals). Samples were subjected to SDS/PAGE analysis using 8% gels and immunoblotted with various antibodies. Enhanced chemiluminescence was used for signal detection (Pierce). As shown in FIG. 6, unstimulated platelets exhibited a subtle level of tyrosine phosphorylation at residues 747 and 759 which presumably reflects weak platelet activation during platelet preparation. As expected, α-thrombin stimulation triggered the tyrosine phosphorylation of integrin β3 at Y747 and Y759. Addition of myr-RGT almost completely abolished phosphorylation of these tyrosines at a peptide concentration of 250 µM. In contrast, neither the scrambled myr-GRT peptide nor the nonmyristoylated RGT peptide plus myristic acid prevented tyrosine phosphorylation at these sites. These data clearly show that myr-RGT attenuated the tyrosine phosphorylation of integrin β3 at Y747 and Y759 suggesting that myr-RGT inhibits the Src-dependent β3 phosphorylation presumably through disrupting the interaction between β3 and Src or, otherwise, the consequent effects of the Src-β3 dissociation such as the inhibitory effect on platelet aggregation.

Example 8

Effect of the RGT Peptide on the Interaction of Platelet Integrin β3 with SH3 Domain of Src To determine whether the RGT peptide interferes with Src interaction with β3, co-immunoprecipitation experiments were completed using platelet lysates in the presence of an excess of the RGT peptide. Experiments were performed using standard immunoprecipitation procedures see, e.g., Arias-Salgado et al., (2003) and Prevost et al., (2005). Briefly, platelets in suspension at $2-4\times10^8$/ml were pre-incubated with peptides (250 µM) for 30 min at 37° C. and lysates were prepared by solubilizing the platelets with cold Nonidet P-40 lysis buffer (1% NP-40, 150 mM NaCl, 50 mM Tris, pH7.2, 1 mM EDTA, 1 mM sodium vanadate, 1 mM PMSF) containing the protease inhibitor mixture. Platelet lysates (600 µg protein) were incubated with a monoclonal antibody against either integrin β3 or Src for 1 h at 4° C. with gentle agitation and were further incubated with protein G-Agarose beads (20 µl) overnight at 4° C. After washing, immunoprecipitates were re-suspended in SDS sample buffer containing 5% 2-mercaptoethanol and subjected to SDS-PAGE analysis using 10% gels. Src, integrin αIIb or β3 subunits was identified by Western blotting using specific monoclonal antibodies.

Figure 7:
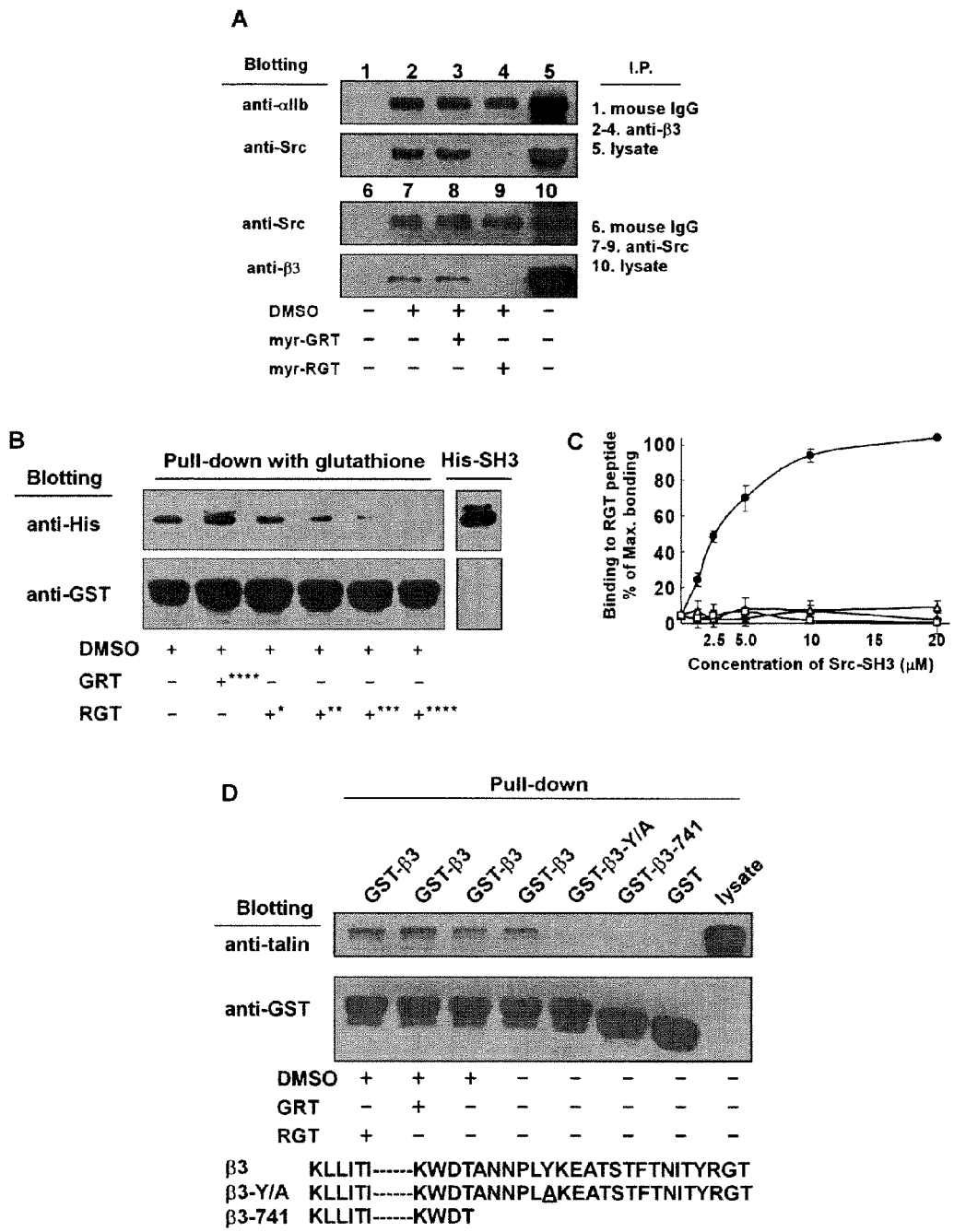
FIG. 7A-D: Effect of myr-RGT on the interaction of integrin β3 cytoplasmic domain with Src or talin.

Results from the immunoprecipitatioin studies are shown in FIG. 7A and demonstrate that Src as well as integrin αIIb, as expected, were co-immunoprecipitated with β3 by an anti-β3 antibody, but not by non-specific control mouse IgG. Preincubation of the platelets with myr-RGT, but not the scrambled peptide, abolished co-immunoprecipitation of β3 with Src but had no effect on the co-immunoprecipitation of αIIb with β3 (FIG. 7). Similar results were obtained in experiments using an anti-Src antibody to precipitate Src-β3 complexes. Addition of RGT peptide to the Src-β3 complex after immunoprecipitation also disrupts Src-β3 association indicating a direct effect of RGT peptide without relying on the platelet cytoplasmic environments.

Further evidence for a direct effect of the RGT peptide on Src-β3 interaction was provided by pull-down experiments using purified recombinant GST-β3 and His-Src-SH3 proteins. The cDNAs encoding the SH3 domain of human c-Src and the wild type or mutant integrin β3 cytoplasmic tail were obtained by PCR amplification and cloned into the pGEX-6P1 vector (Amersham) downstream of the GST sequence. The Src-SH3 cDNA was also inserted into the pET32A vector (Novagen). All constructs were verified by DNA sequencing. Wild type or mutated GST-β3 cytoplasmic tail fusion proteins (GST-β3, GST-β3Y/A, GST-β3-741) were expressed in *E. coli* (Arias-Salgado et al., 2005) and purified from bacterial lysates by batch elution from glutathione-Sepharose. Purified GST fusion proteins coupled to glutathione-Sepharose 4B beads were incubated for 1 h at 4° C. with platelet lysates in RIPA buffer (50 mM Tris, pH7.4, 75 mM NaCl, 1% NP-40, 0.5% deoxycholic acid, 0.1% SDS, 5 mM EDTA, 1 mM sodium vanadate and the protease inhibitor mixture) in the presence or absence of the peptide, and immunoblotted with specific antibodies. His-tagged Src-SH3 was expressed in BL21 (DE3) and purified by Ni-affinity chromatography. For β3-Src-SH3 pull-down assays, immobilized wild type GST-β3 was incubated with His-Src-SH3 in the presence of increasing concentrations of the RGT peptide overnight at 4° C. under constant rotation. Complexes were washed and subjected to Western blot analysis.

Results of the pull-down studies are shown in FIG. 7B and demonstrate that RGT peptide dose-dependently inhibited Src-SH3 binding to the integrin β3 tail. These results suggest that the binding of RGT directly induces dissociation of Src from integrin β3. As a proof of this hypothesis, FIG. 7C depicts a direct binding of GST-Src-SH3 recombinant protein to immobilized RGT peptide. This binding was dose-dependent and almost reached saturation at a protein concentration of 20 µM. The specificity of the binding was evidenced by the negative reaction of GST-Src-SH3 with the scrambled GRT peptide. These data established that Src interaction with integrin β3 was abrogated by myr-RGT which competes with β3 tail for binding Src. On the other hand, talin was positively detected in a GST-integrin β3 cytoplasmic domain pull-down experiment. Unlike the integrin β3-Src interaction, the RGT peptide could not affect integrin β3-talin interaction (FIG. 7D). As controls, mutant integrin β3 cytoplasmic domains lacking the talin head binding site or bearing a point mutation which is known to disrupt integrin β3-talin interaction, β3-741 and β3-Y/A, were unable to pull-down talin. These results indicate that the RGT peptide had no effect on talin binding to the integrin β3 cytoplasmic domain.

Example 9

Stimulatory Effect of myr-RGT on Clot Retraction in Human Platelet Rich Plasma

Figure 8:
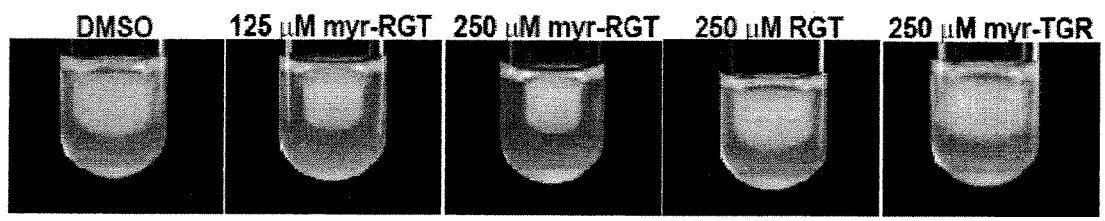
FIG. 8: Stimulatory effect of myr-RGT on clot retraction in human platelet rich plasma. Blood was freshly drawn from healthy donors and anti-coagulated with $\frac{1}{10}^{th}$ volume of 3.8% risodium citrate. Platelet-rich plasma (PRP) was isolated from red and white cells by centrifugation. PRP was preincubated with indicated concentrations of myr-RGT or control peptides before adding thrombin to initiate coagulation. After incubation, the clots were photographed.

Human platelet-rich plasma (PRP) was used to determine whether myr-RGT can induce clot retraction. Blood was freshly drawn from healthy donors and anti-coagulated with $\frac{1}{10}^{th}$ volume of 3.8% trisodium citrate. PRP was isolated from red and white cells by centrifugation and was preincubated with indicated concentrations of myr-RGT or control substance before adding thrombin to initiate coagulation. After incubation, the clots were photographed. A reproduction of clot photographs is shown in FIG. 8. Incubation of PRP with 125 µM myr-RGT and to a greater extent with 250 µM myr-RGT markedly reduced clot size. In contrast, DMSO alone, unconjugated RGT (250 µM) and myr-TGR (250 µM) all failed have any noticeable effect on clot size. Taken together these studies indicate that myr-RGT may be used in therapies to mediate clot retraction.

REFERENCES

Each of the foregoing references are incorporated herein in their entirety.

U.S. Pat. No. 4,529,596
U.S. Pat. No. 5,036,156
U.S. Pat. No. 5,576,328
U.S. Pat. No. 6,080,875
U.S. Pat. No. 6,180,793
U.S. Pat. No. 6,258,961
Angelillo-Scherrer et al., "Role of Gas6 receptors in platelet signaling during thrombus stabilization and implications for antithrombotic therapy," *J. Clin. Invest.* 115:237-246, 2005.
Arias-Salgado et al., "Src kinase activation by direct interaction with the integrin beta cytoplasmic domain," *Proc. Natl. Acad. Sci. U.S.A.*, 100:13298-13302, 2003.
Arias-Salgado et al., "Specification of the direction of adhesive signaling by the integrin beta cytoplasmic domain," *J. Biol. Chem.*, 280:29699-29707, 2005.
Bangham et al., *J. Mol. Biol.*, 13(1):253-259, 1965.
Bassler et al., "A mechanistic model for paradoxical platelet activation by ligand-mimetic alphaIIb beta3 (GPIIb/IIIa) antagonists," *Arterioscler. Thromb. Vasc. Biol.*, 27:e9-15, 2007.

Dai et al., "A critical role for 14-3-3zeta protein in regulating the VWF binding function of platelet glycoprotein Ib-IX and its therapeutic implications," *Blood,* 106:1975-1981, 2005.

Deamer and Uster, In: Liposome Preparation: Methods and Mechanisms, Ostro (Ed.), Liposomes, 1983.

Flevaris et al., "A molecular switch that controls cell spreading and retraction," *J. Cell. Biol.* 179:553-565, 2007.

Ginsberg et al., "Inhibition of fibronectin binding to platelets by proteolytic fragments and synthetic peptides which support fibroblast adhesion," *J. Biol. Chem.,* 260:3931-3936, 1985.

Hers et al., "Inhibition of platelet integrin alpha(IIb)beta(3) by peptides that interfere with protein kinases and the beta(3) tail," *Arterioscler. Thromb. Vasc. Biol.,* 20:1651-1660, 2000.

Hynes, "Integrins: bidirectional, allosteric signaling machines," *Cell,* 110:673-687, 2002.

Ginsberg M H, Partridge A, Shattil S J. Integrin regulation. Curr. Opin.Cell Biol. 2005; 17:509-516.

Gregoriadis, In: Drug Carriers in Biology and Medicine, Gregoriadis (Ed.), 287-341, 1979.

Larkin et al., "ICln, a novel integrin alphaIIbbeta3-associated protein, functionally regulates platelet activation," *J. Biol. Chem.,* 279:27286-27293, 2004.

Law et al., "Outside-in integrin signal transduction. Alpha IIb beta 3-(GP IIb IIIa) tyrosine phosphorylation induced by platelet aggregation," *J. Biol. Chem.* 271:10811-10815, 1996.

Law et al., "Integrin cytoplasmic tyrosine motif is required for outside-in alphaIIbbeta3 signalling and platelet function," *Nature,* 401:808-811, 1999.

Li et al. "A mitogen-activated protein kinase-dependent signaling pathway in the activation of platelet integrin alpha IIbbeta3," *J. Biol. Chem.,* 276:42226-42232, 2001.

Li et al., "A platelet secretion pathway mediated by cGMP-dependent protein kinase," *J. Biol. Chem.* 279:42469-42475, 2004.

Liu et al., "Identification of a functionally important sequence in the cytoplasmic tail of integrin beta 3 by using cell-permeable peptide analogs," *Proc. Natl. Acad. Sci. U.S.A.,* 93:11819-11824, 1996.

Liu et al. "The beta3 subunit of the integrin alphaIIbbeta3 regulates alphaIIb-mediated outside-in signaling," *Blood,* 105:4345-4352, 2005.

Litjens et al., "Involvement of the beta3 E[749]ATSTFTN[756] region in stabilizing integrin alphaIIbbeta3-ligand interaction," *J. Thromb. Haemost.,* 1:2216-2224, 2003[1].

Litjens et al. "Cytoplasmic regions of the beta3 subunit of integrin alphaIIbbeta3 involved in platelet adhesion on fibrinogen under flow conditions," *J. Thromb. Haemost.* 1:2014-2021, 2003[2].

Martin et al., "A palmitylated peptide derived from the glycoprotein Ib beta cytoplasmic tail inhibits platelet activation," *J. Thromb. Haemost.,* 1:2643-2652, 2003.

Obergfell et al., "Coordinate interactions of Csk, Src, and Syk kinases with [alpha]IIb[beta]3 initiate integrin signaling to the cytoskeleton," *J. Cell. Biol.,* 157:265-275, 2002.

Osdoit et al., "Fibrin clot retraction by human platelets correlates with alpha(IIb)beta(3) integrin-dependent protein tyrosine dephosphorylation," *J. Biol. Chem.,* 276:6703-6710, 2001.

Phillips et al., "Therapeutic approaches in arterial thrombosis," *J. Thromb. Haemost.,* 3:1577-1589, 2005.

Podolnikova et al., "Identification of a novel binding site for platelet integrins alpha IIb beta 3 (GPIIbIIIa) and alpha 5 beta 1 in the gamma C-domain of fibrinogen," *J. Biol. Chem.,* 278:32251-32258, 2003.

Prevost et al., "Signaling by ephrinB1 and Eph kinases in platelets promotes Rap1 activation, platelet adhesion, and aggregation via effector pathways that do not require phosphorylation of ephrinB1," *Blood* 103:1348-1355, 2004.

Prevost et al., "Eph kinases and ephrins support thrombus growth and stability by regulating integrin outside-in signaling in platelets," *Proc. Natl. Acad. Sci. U.S.A.,* 102: 9820-9825, 2005.

Remington's Pharmaceutical Sciences, 18th Ed. Mack Printing Company, 1990.

Shattil et al., "Integrin signaling: the platelet paradigm," *Blood* 91:2645-2657, 1998.

Szoka and Papahadjopoulos, *Proc. Natl. Acad. Sci. U.S.A.,* 75:4194-4198, 1978.

Stephens et al., "A sequence within the cytoplasmic tail of GpIIb independently activates platelet aggregation and thromboxane synthesis," *J. Biol. Chem.* 273:20317-20322, 1998.

Su et al., "RGT, a synthetic peptide corresponding to the integrin beta 3 cytoplasmic C-terminal sequence, selectively inhibits outside-in signaling in human platelets by disrupting the interaction of integrin alpha IIb beta 3 with Src kinase," *Blood,* 112:592-602, 2008.

Tadokoro et al., "Talin binding to integrin beta tails: a final common step in integrin activation," *Science* 302:103-106, 2003.

Tsuboi, "Calcium integrin-binding protein activates platelet integrin alpha IIbbeta 3," *J. Biol. Chem.,* 277:1919-1923, 2002.

Vinogradova et al., "A structural basis for integrin activation by the cytoplasmic tail of the alpha IIb-subunit," *Proc. Natl. Acad. Sci. U.S.A.,* 97:1450-1455, 2000.

Vinogradova et al., "A structural mechanism of integrin alpha (IIb)beta(3) "inside-out" activation as regulated by its cytoplasmic face," *Cell,* 110:587-597, 2002.

Wang et al., "Platelet alpha2beta1 integrin activation: contribution of ligand internalization and the alpha2-cytoplasmic domain," *Blood,* 102:1307-1315, 2003.

Xi et al., "Critical roles for the COOH-terminal NITY and RGT sequences of the integrin beta3 cytoplasmic domain in inside-out and outside-in signaling," *J. Cell. Biol.,* 162: 329-339, 2003.

Xi et al. "Tyrosine phosphorylation of the integrin beta3 subunit regulates beta3 cleavage by calpain," *J. Biol. Chem.,* 281:29426-29430, 2006.

What is claimed is:

1. A composition comprising a peptide consisting of the amino acid sequence RGT and a lipid covalently bound to the amino-terminus of said peptide.

2. The composition of claim 1, wherein the lipid is a fatty acid.

3. The composition of claim 2, wherein the fatty acid is a saturated fatty acid.

4. The composition of claim 3, wherein the saturated fatty acid is a myristic acid or palmitic acid.

5. The composition of claim 4, wherein the saturated fatty acid is myristic acid.

6. A pharmaceutical composition comprising a composition according to claim 1 in a pharmaceutically acceptable carrier.

7. A method for inhibiting platelet aggregation in a subject comprising administering to the subject the composition of claim 1, said composition administered in an amount effective to inhibit platelet aggregation.

8. The method of claim 7, wherein the lipid is a fatty acid.

9. The method of claim 8, wherein the fatty acid is a saturated fatty acid.

10. The method of claim 9, wherein the saturated fatty acid is a myristic acid or palmitic acid.

11. The method of claim 9, wherein the saturated fatty acid is myristic acid.

12. The method of claim 7, wherein the RGT peptide inhibits or reduces phosphorylation of integrin β3 in a platelet cell.

13. The method according to claim 7, further comprising administering a therapeutic drug to the subject before, after or concurrently with the composition.

14. The method according to claim 13, wherein the therapeutic drug is clopidogrel, ticlopidine, cilostazol, abciximab, eptifibatide, tirofiban, defibrotide, dipyridamole or aspirin.

15. The method of claim 7, wherein the subject has atherosclerosis.

16. The method of claim 7, wherein, the composition is administered to the subject by oral, nasal, topical, orthotopic, intradermal, subcutaneous, intramuscular, intraperitoneal or intravenous administration.

17. The method of claim 16, wherein the composition administered to a subject by intravenous administration.

18. The method of claim 7, wherein the composition further comprises a pharmaceutically acceptable carrier.

19. A method for reducing the occurrence of a secondary ischemic event in a subject comprising administering to a subject who has suffered a primary ischemic event a therapeutically effective amount of the composition of claim 1.

20. The method of claim 19, wherein the primary and/or secondary ischemic event is angina, reocclusion after percutaneous transluminal coronary angioplasty, restenosis, thrombotic stroke, transient ischemic attack, reversible ischemic neurological deficit or intermittent claudication.

21. A method for reducing the size of a blood clot in a subject comprising administering to the subject the composition of claim 1, said composition administered in an amount effective to reduce the size of a blood clot.

22. The method of claim 21, wherein the lipid is a fatty acid.

23. The method of claim 22, wherein the fatty acid is a saturated fatty acid.

24. The method of claim 22, wherein the saturated fatty acid is a myristic acid or palmitic acid.

25. The method of claim 24, wherein the saturated fatty acid is myristic acid.

26. The method of claim 21, wherein the RGT amino acid sequence inhibits or reduces phosphorylation of integrin β3 in a platelet cell.

27. The method according to claim 21, further comprising administering a therapeutic drug to the subject before, after or concurrently with the composition.

28. The method according to claim 27, wherein the therapeutic drug is an anticoagulant.

29. The method according to claim 28, wherein the anticoagulant is warfarin, acenocoumarol, phenprocoumon, phenindione, heparin, fondaparinux, idraparinux, argatroban, lepirudin, bivalirudin or dabigatran.

30. The method according to claim 27, wherein the therapeutic drug is a thrombolytic drug.

31. The method according to claim 30, wherein the thrombolytic drug is streptokinase, tissue plasminogen activator (tPA), urokinase, Reteplase, tenecteplase, anistreplase or brinase.

32. The method of claim 21, wherein, the composition is administered to the subject by oral, nasal, topical, orthotopic, intradermal, subcutaneous, intramuscular, intraperitoneal or intravenous administration.

33. The method of claim 32, wherein the composition is administered to the subject by intravenous administration.

34. The method of claim 21, wherein the composition further comprises a pharmaceutically acceptable carrier.

35. The method of claim 21, wherein the subject has pulmonary embolism, venous thrombosis, deep vein thrombosis, portal vein thrombosis, renal vein thrombosis, jugular vein thrombosis, Budd-Chiari syndrome, Paget-Schroetter disease, cerebral venous sinus thrombosis, arterial thrombosis, thrombotic stroke or myocardial infarction.

* * * * *